(12) United States Patent
Kersten et al.

(10) Patent No.: US 11,396,548 B2
(45) Date of Patent: *Jul. 26, 2022

(54) EGFR TARGETED THERAPY OF NEUROLOGICAL DISORDERS AND PAIN

(71) Applicant: Sykehuset Sørlandet HF, Kristiansand (NO)

(72) Inventors: Christian Kersten, Kristiansand (NO); Marte Grønlie Cameron, Kristiansand (NO); Svein Mjåland, Kristiansand S (NO)

(73) Assignee: Sykehuset Sørlandet HF, Kristiansand (NO)

( * ) Notice: Subject to any disclaimer, the term of this patent is extended or adjusted under 35 U.S.C. 154(b) by 65 days.

This patent is subject to a terminal disclaimer.

(21) Appl. No.: 16/824,108

(22) Filed: Mar. 19, 2020

(65) Prior Publication Data

US 2020/0216547 A1 Jul. 9, 2020

Related U.S. Application Data

(63) Continuation of application No. 15/270,525, filed on Sep. 20, 2016, now Pat. No. 10,611,844, which is a continuation of application No. 14/654,180, filed as application No. PCT/EP2013/003931 on Dec. 20, 2013, now abandoned.

(60) Provisional application No. 61/740,876, filed on Dec. 21, 2012.

(51) Int. Cl.
| | |
|---|---|
| *A61K 39/395* | (2006.01) |
| *A61K 45/06* | (2006.01) |
| *A61K 31/517* | (2006.01) |
| *A61K 31/5377* | (2006.01) |
| *A61P 25/02* | (2006.01) |
| *A61K 39/00* | (2006.01) |
| *A61P 29/00* | (2006.01) |
| *C07K 16/28* | (2006.01) |
| *A61K 9/00* | (2006.01) |

(52) U.S. Cl.
CPC ........ *C07K 16/2863* (2013.01); *A61K 9/0019* (2013.01); *A61K 9/0053* (2013.01); *A61K 31/517* (2013.01); *A61K 31/5377* (2013.01); *A61K 39/3955* (2013.01); *A61K 45/06* (2013.01); *A61P 25/02* (2018.01); *A61K 2039/505* (2013.01); *A61K 2039/54* (2013.01); *A61K 2039/545* (2013.01); *A61K 2039/55* (2013.01); *A61P 29/00* (2018.01); *C07K 2317/21* (2013.01); *C07K 2317/24* (2013.01); *C07K 2317/76* (2013.01)

(58) Field of Classification Search
CPC ............ C07K 16/2863; C07K 2317/21; C07K 2317/24; C07K 231/76; A61K 9/0019; A61K 9/0053; A61K 31/517; A61K 31/5377; A61K 39/3955; A61K 2039/505; A61K 2039/54; A61K 2039/545; A61K 2039/55; A61K 45/06; A61K 2300/00; A61P 25/02; A61P 29/00

See application file for complete search history.

(56) References Cited

U.S. PATENT DOCUMENTS

| | | |
|---|---|---|
| 5,223,409 A | 6/1993 | Ladner |
| 5,565,332 A | 10/1996 | Hendricuhendricus |
| 5,585,089 A | 12/1996 | Queen |
| 5,824,544 A | 10/1998 | Armentano |
| 5,830,730 A | 11/1998 | German |
| 5,872,154 A | 2/1999 | Wilson |
| 5,885,808 A | 3/1999 | Spooner |
| 5,906,820 A | 5/1999 | Bacha |
| 5,981,225 A | 11/1999 | Kochanek |
| 5,994,106 A | 11/1999 | Kovesdi |
| 5,994,128 A | 11/1999 | Fallaux |
| 5,994,132 A | 11/1999 | Chamberlain |
| 6,001,557 A | 12/1999 | Wilson |
| 6,019,978 A | 2/2000 | Ertl |
| 6,033,908 A | 3/2000 | Bout |
| 6,054,297 A | 4/2000 | Carter |
| 6,180,370 B1 | 1/2001 | Queen |
| 6,506,559 B1 | 1/2003 | Fire |
| 7,893,036 B2 | 2/2011 | Zamore |
| 8,481,064 B2 | 7/2013 | McKay |
| 2008/0025958 A1 | 1/2008 | Hannon |

(Continued)

FOREIGN PATENT DOCUMENTS

| | | |
|---|---|---|
| JP | 1-2007-532566 | 11/2007 |
| WO | WO 00/09675 | 2/2000 |
| WO | WO 00/12738 | 3/2000 |

(Continued)

OTHER PUBLICATIONS

Swanson CD et al. Inhibition of epidermal growth factor receptor tyrosine kinase ameliorates collagen-induced arthritis. J. Immunol. 2012, 188: 3513-3521. (Year: 2012).*

(Continued)

*Primary Examiner* — Kimberly Ballard
(74) *Attorney, Agent, or Firm* — Casimir Jones S.C.; J. Mitchell Jones

(57) ABSTRACT

The present invention relates to compositions and methods for treatment of neurological disorders. In particular, the present invention relates to the epidermal growth factor receptor (EGFR) as a clinical target for treatment of neurological disorders, preferably in conjunction with neuropathic pain. The invention relates in more detail to compositions comprising inhibitors of EGFR.

18 Claims, 6 Drawing Sheets

(56) References Cited

U.S. PATENT DOCUMENTS

Figure 3:
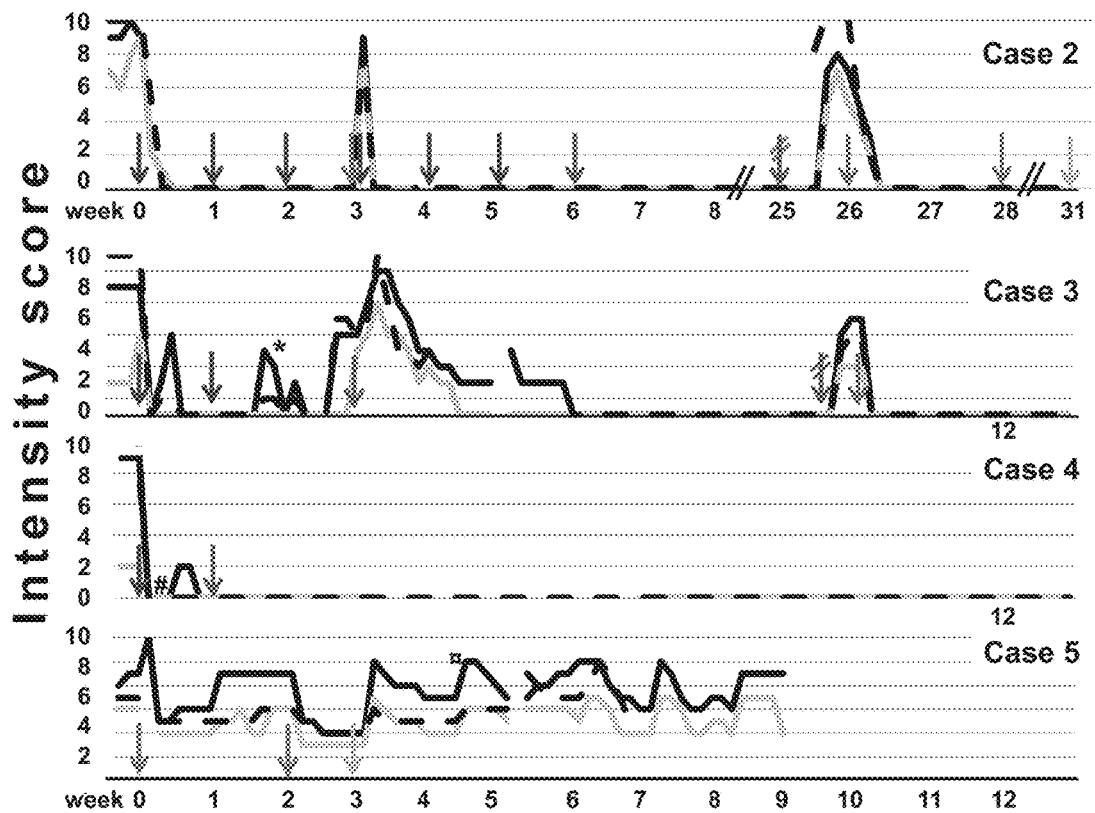

| | | |
|---|---|---|
| 2008/0269147 A1 | 10/2008 | Tuschl |
| 2012/0094999 A1 | 4/2012 | Gray et al. |

FOREIGN PATENT DOCUMENTS

| | | |
|---|---|---|
| WO | WO 01/98537 | 12/2001 |
| WO | WO 03/070966 | 8/2003 |
| WO | WO 2005/023783 | 3/2005 |
| WO | WO 05/038054 | 4/2005 |
| WO | WO 05/054270 | 6/2005 |
| WO | WO 2005/099756 | 10/2005 |
| WO | WO 06/066048 | 6/2006 |
| WO | WO 08/006369 | 1/2008 |
| WO | WO 08/043753 | 4/2008 |
| WO | WO 08/051306 | 5/2008 |
| WO | WO2009/048947 | 4/2009 |
| WO | WO 2012/156437 | 11/2012 |
| WO | WO 2013/005108 | 1/2013 |

OTHER PUBLICATIONS

Alvarenga et al. "In-depth biophysical analysis of interactions between therapeutic antibodies and the extracellular domain of the epidermal growth factor receptor." Anal Biochem 2012;421:138-51.
Andres et al.: Quantitative automated microscopy (QuAM) elucidates growth factor specific signalling in pain sensitization, Molceular Pain 2010, 6:98.
Atalay et al., Novel therapeutic strategies targeting the epidermal growth factor receptor (EGFR) family and its downstream effectors in breast cancer. Ann Oncol 2003, 14:1346-1363.
Bohula et al., "RNA: Structure Metabolism and Catalysis: The Efficacy of Small Interfering RNAs Targeted to the Type 1 . . . " (J. Biol. Chem., 2003; 278: 15991-15997.
Bouhassira et al. "Prevalence of chronic pain with neuropathic characteristics in the general population." Pain 2008;136:380-7.
Breivik et al. "A new treatment principle for neuropathic pain? Approved oncologic drugs: Epidermal growth factor receptor (EGFR) inhibitors dramatically relieve severe neuropathic pain in a case series" Scandinavian Journal of Pain, vol. 4, No. 1, 2013, pp. 1-2.
Brown et al. "Gefitinib for the first-line treatment of locally advanced or metastatic non-small cell lung cancer." Health Technol Assess 2010;14:71-9.
Brummelkamp et al, "A System for Stable Expression of Short Interfering RNAs in Mammalian Cells," Science 2002; 296:550-3.
Calvo et al. "Following nerve injury neuregulin-1 drives microglial proliferation and neuropathic pain via the MEK/ERK pathway." Glia 2011;59:554-68.
Caplen et al, "Specific inhibition of gene expression by small double-stranded RNAs in invertebrate and vertebrate systems," Proc Natl Acad Sci U.S.A. 2001; 98: 9742-7.
Carell et al., "*A Novel Procedure for the Synthesis of Libraries Containing Small Organic Molecules*," Angew. Chem. Int. Ed. Engl. 33:2059-2061 [1994].
Carroll et al. "Expression of neuregulins and their putative receptors, ErbB2 and ErbB3, is induced during Wallerian degeneration." J Neurosci 1997;17:1642-59.
Chen-Plotikin et al., "Plasma EGF Levels predict cognitive decline in Parkinson's Disease" Ann Neurol. Apr. 2011;69(4):655-63.
Cho et al., "An Unnatural Biopolymer" Science 261:1303 [1993].
Ciardiello et al., Interaction between the epidermal growth factor receptor (EGFR) and the vascular endothelial growth factor (VEGF) pathways: a rational approach for multi-target anticancer therapy. Ann Oncol 2006, 17(Suppl 7):vii109-114.
Crips, C., et al., "Epidermal growth factor receptor targeted therapy in stages III and IV head and neck cancer," Jun. 2010, Current Oncology, Jun. 2010, vol. 17, No. 3, pp. 37-48.
Cull et al., "Screening for receptor ligands using large libraries of peptides linked to the C terminus of the lac repressor," Proc. Nad. Acad. Sci. USA 89:18651869 [1992].

Cwirla et al., "Peptides on phage: A vast library of peptides for identifying ligands," Proc. Natl. Acad. Sci. 87:6378-6382 [1990].
Devlin et al., "Random Peptide Libraries: A Source of Specific Protein Binding Molecules," Science 249:404-406 [1990].
Dewitt et al., "Diversomers: An approach to nonpeptide, nonoligomeric chemical diversity," Proc. Natl. Acad. Sci. U.S.A. 90:6909-6913 [1993].
Dieleman et al. "Incidence rates and treatment of neuropathic pain conditions in the general population." Pain 2008;137:681-8.
Dragnev et al., Bexarotene and erlotinib for aerodigestive tract cancer. J Clin Oncol 2005, 23:8757-8764.
Dworkin et al. "An overview of neuropathic pain: syndromes, symptoms, signs, and several mechanisms." Clin J Pain 2002;18:343-9.
Elbashir et al., "Functional anatomy of siRNAs for mediating efficient RNAi in *Drosophila* melanogaster embryo lysate," EMBO J. 2001; 20: 6877-88.
Elbashir et al., "RNA interference is mediated by 21-and 22-nucleotide RNAs" Genes Dev. 2001;15: 188-200.
Elbashir et al., "Duplexes of 21-nucleotide RNAs mediate RNA interference in cultured mammalian cells" Nature. 2001; 411:494-8.
Erschbamer et al.,"Inhibitiing Epidermal Growth Factor Receptof Improves Structural, Locomotor, Sensory and Bladder Recovery from Experimental Spinal Cord Injury" The Journal of Neuroscience, Jun. 13, 2007 27(24):6428-6435.
Erb et al., "Recursive deconvolution of combinatorial chemical libraries" Proc. Nad. Acad. Sci. USA 91:11422-11426 [1994].
Felici, J. "Selection of Antibody Ligands from a Large Library of Oligopeptides Expressed on a Multivalent Exposition Vector" Mol. Biol. 222:301 [1991].
Finnerup et al. "The evidence for pharmacological treatment of neuropathic pain." Pain 2010;150:573-81.
Fodor "Multiplexed biochemical assays with biological chips" Nature 364:555-556 [1993].
Folprecht et al: Phase I pharmacokinetic/pharmacodynamic study of EKB-569, an irreversible inhibitor of the epidermal growth factor receptor tyrosine kinase, in combination with irinotecan, 5-fluorouracil, and leucovorin (FOLFIRI) in first-line treatment of patients with metastatic colorectal cancer. Clin Cancer Res 2008,14:215-223.
Gallop et al., "Applications of Combinatorial Technologies to Drug Discovery" J. Med. Chem. 37:1233 [1994].
Hofstetter et al. "Allodynia limits the usefulness of intraspinal neural stem cell grafts; directed differentation improves outcome." Nature Neuroscience, 2005, vol. 8, No. 3, pp. 346-353.
Holen et al, "Positional effects of short interfering RNAs targeting the human coagulation trigger Tissue Factor" Nucleic Acids Res. 2002; 30:1757-66.
Holt K. "Common side effects and interactions of colorectal cancer therapeutic agents." J Pract Nurs 2011;61:7-20.
Houghton "The Use of Synthetic Peptide Combinatorial Libraries for the Identification of Bioactive Peptides" Biotechniques 13:412-421 [1992].
International Search Report and Written Opinion dated Dec. 12, 2012, PCT/IB2012/001619.
International Search Report and Written Opinion dated Apr. 4, 2014, PCT/EP2013/003931.
Ise et al. "Overexpressed HER2 in NSCLC is a possible therapeutic target of EGFR inhibitors." Anticancer Res 2011;31:4155-62.
Overhoff et al., "Local RNA Target Structure Influences siRNA Efficacy: A Systematic Global Analysis" J Mol Biol. May 13, 2005;348(4):871-881.
Osawa et al., "Two Cases of Colorectal Cancer Patients with Poor Performance Status Who Had Unresectable Liver Metastasis Effectively treated by Cetuximab", Japan J. Cancer Chemotherapy, 2010, 37(11): 2189-2191.
Jensen et al. "The impact of neuropathic pain on health-related quality of life: review and implications" Neurology 2007;68:1178-82.
Jensen et al. "A new definition of neuropathic pain" Pain 2011;152:2204-5.
Ji RR. "Mitogen-activated protein kinases as potential targets for pain killers" Curr Opin Investig Drugs 2004;5:71-5.
Ji et al. "MAP kinase and pain" Brain Res Rev 2009;60(1):135-48.

(56) References Cited

OTHER PUBLICATIONS

Kanzaki et al. "Expression changes of the neuregulin 1 isoforms in neuropathic pain model rats." Neurosci Lett 2012;508:78-83.
Kersten et al., "Cetuximab alleviates neuropathic pain despite tumour progression," 2012, BMJ Case Reports 2012, vol. 2012.
Kersten et al. "Epithelial growth factor receptor (EGFR)—inhibition for relief of neuropathic pain—A case series", Scandinavian Journal of Pain, vol. 4, No. 1, 2013, pp. 3-7.
Lam "Application of combinatorial library methods in cancer research and drug discovery" Anticancer Drug Des., 1997, 12:145-167.
Lam "A new type of synthetic peptide library for identifying ligand-binding activity" Nature 354:82-84 [1991].
Maklad et al. "The EGFR is required for proper innervation to the skin" J. Invest. Dermatol. 2009;129(3):690-8.
Maughan et al. "Addition of cetuximab to oxaliplatin-based first-line combination chemotherapy for treatment of advanced colorectal cancer: results of the randomised phase 3 MRC COIN trial." Lancet 2011;377:2103-14.
Mesia Ricard et al., "Rapid palliation of symptoms with platinum-based chemotherapy plus cetuximab in recurrent oral cancer: a case report," Head & Neck Oncology, Biomed Central Ltd., London, UK, vol. 2, No. 1, Jan. 27, 2010, p. 3.
Nautiyal et al. "Emerging therapies in gastrointestinal cancers." World journal of gastroenterology : WJG 2006;12:7440-50.
Scuteri et al. "NGF protects dorsal root ganglion neurons from oxaliplatin by modulating JNK/Sapk and ERK1/2." Neurosci Lett. Dec. 17, 2010;486(3):141-5. Epub Sep. 17, 2010. PMID:20850503.
Kretschmer-Kazemi, et al., "The activity of siRNA in mammalian cells is related. . ." Nucleic Acids Res. Aug. 1, 2003;31(15):4417-24.
Oliveras-Ferraros et al. "Interferon/STAT1 and neuregulin signaling pathways are exploratory biomarkers of cetuximab (Erbitux(R)) efficacy in KRAS wild-type squamous carcinomas: a pathway-based analysis of whole human-genome microarray data from cetuximab-adapted tumor cell-line models." Int J Oncol 2011;39:1455-79.
Oyagi et al., "Forebrain specific heparin-binding epidermal growth . . ." Neuroscience. Jun. 30, 2011;185:116-24.
Petrelli et al. "Efficacy of EGFR Tyrosine Kinase Inhibitors in Patients With EGFR-Mutated Non-Small-Cell Lung Cancer: A Meta-Analysis of 13 Randomized Trials." Clin Lung Cancer 2012;13:107-14.
Ramanathan RK. "Alternative dosing schedules for cetuximab: a role for biweekly administration?" Clin Colorectal Cancer 2008;7:364-8.
Saadeh et al. "Panitumumab: a fully human monoclonal antibody with activity in metastatic colorectal cancer." Ann Pharmacother 2007;41:606-13.
Schamel et al. "Signal transduction: specificity of growth factors explained by parallel distributed processing" Med Hypotheses 1996;47:249-55.
Scholz et al. "The neuropathic pain triad: neurons, immune cells and glia" Nat Neurosci 2007;10:1361-8.
Liu et al. "Activation of epidermal growth factor receptors in astrocytes: from development to neural injury" J Neurosci Res 2007;85:3523-9.
Scott and Smith, "Searching for peptide ligands with an epitope library." Science 249:386-390 [1990].
Sohail et al, "Antisense oligonucleotides selected by hybridization . . ." Nucleic Acids Res., 2001; 29(10): 2041-2045.
Vincenzi et al. "The biological properties of cetuximab." Nov. 2008;68(2):93-106. Epub Aug. 3, 2008. Review.
Tuschl and Borkhardt, "Small interfering RNAs: a revolutionary tool for the analysis of gene function and gene therapy." Intervent. 2002; 2(3):158-67.
Tveit et al. "Randomized phase III study of 5-Fluouracil/Folinate/Oxaliplatin given continously or intermittently with or witout cetuximab: The Nordic VII Study (NCT00145314)." Ann Oncol 2010;21:viii1-viii12.
Vincenzi et al. "Cetuximab: from bench to bedside" Curr Cancer Drug Targets 2010;10:80-95.
Werner et al. "Localization of immunoreactive epidermal growth factor receptors in human nervous system" J. Histochem. Cytochem. 1988;36(1):81-6.
Wheeler et al. "Understanding resistance to EGFR inhibitors-impact on future treatment strategies." Nature reviews Clinical oncology 2010;7:493-507.
Xiang et al., "Short hairpin RNA-expressing bacteria elicit RNA interference in mammals." Nature 24: 6 (2006).
Xiong, H.Q., et al., "Cetuximab, A Monoclonal Antibody Targeting the Epidermal Growth Factor Receptor, in Combination with Gemcitabine for Advanced Pancreatic Cancer: A Multicenter Phase II Trial," Journal of Clinical Oncology, American Society of Clinical Oncology, US, vol. 22, No. 13, Jul. 1, 2004, pp. 2610-2616.
Yasuda et al "p38 MAP kinase inhibitors as potential therapeutic drugs for neural diseases" Cent Nerv Syst Agents Med Chem 2011;11:45-59.
Zuckennann et al., "Discovery of Nanomolar Ligands for o7-Transmembrane G-Protein-Coupled Receptors from a Diverse . . ." J. Med. Chem. 37: 2678-85 [1994].
Huang, Shyhmin et al. Dual-Agent Molecular Targeting of the Epidermal Growth Factor Receptor (EGFR): Combining Anti-EGFR Antibody with Tyrosine Kinase Inhibitor, Cancer Research, Aug. 2004, vol. 64, No. 15, p. 5355-5362.
Notice of Reasons for Refusal, Japanese Patent Application No. 2018-197322, dated Dec. 9, 2019, 4 pages.
Boland, BA et al. Chemotherapy-induced neuropathy in cancer survivors. 2010, vol. 24, issue 2, from cancernetwork.com, retrieved Sep. 11, 2019, 3 web-based pages. (Year 2010).
Janjigian, YY et al. "Phase I/II trial of cetuximab and erlotinib in patients with lung adenocarcinoma and acquired resistance to erlotinib." Clin. Cancer Res. 2011, 17(8): 2521-2527.
Ramalingam, S. et al. Dual inhibition of the epidermal growth factor receptor with cetuximab, an IgG1 monoclonal antibody, and gefitinib, a tyroskine kinase inhibitor, in patients with refractory non-small cell lung cancer (NSCLC): a phase 1 study. J. Thoracic Oncology, 2008, 3(3): 258-264.
Simmons, CPL et al. "Clinical management of pain in advance lung cancer." Clinical Medicine Insights: Oncology, 2012, 6:331-346.
Erlotinib fact sheet, Chemocare.com, retrieved from internet Apr. 1, 2019.
Moyer M. Metals in medicine and the environment; Peripheral nueropathy and metals. Last modified Aug. 2009. Retrieved from faculty.virgina.edu/metals/cases/moyer2.html on May 27, 2018, 5 pages.

\* cited by examiner

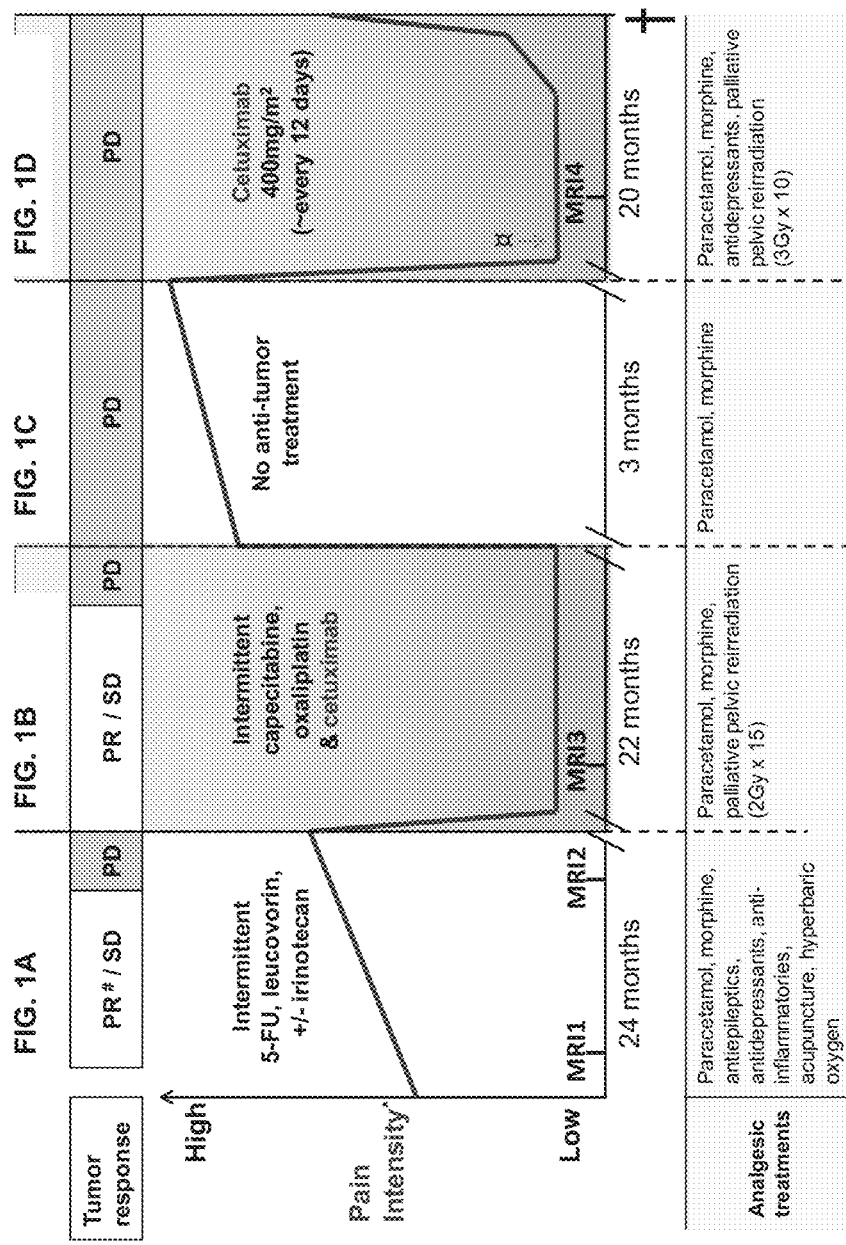

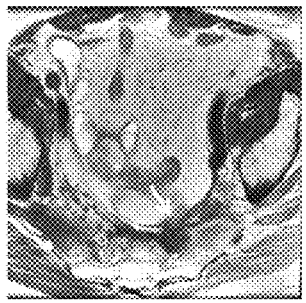

FIG. 2A MRI taken three months prior to starting capecitabine, oxaliplatin and cetuximab (corresponds to MRI 2 in figure 1a). There is a presacral recurrence that extends along the left sciatic nerve

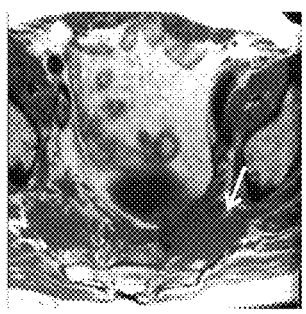
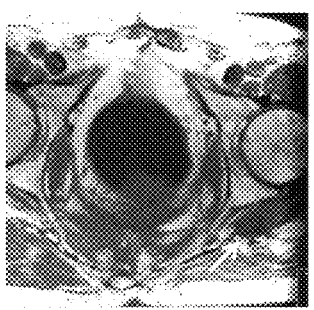

FIG. 2B MRI taken 4 months after starting capecitabine, oxaliplatin and cetuximab (corresponds to MRI 3 in figure 1b). Both the presacral recurrence and its extension along the sciatic nerve have increased in size.

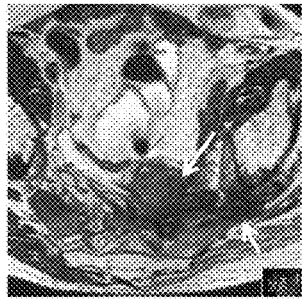
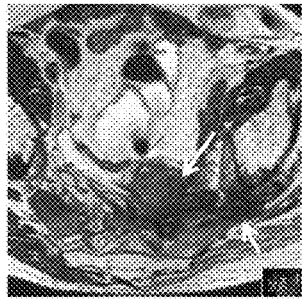

FIG. 2C MRI taken eight months after starting cetuximab monotherapy for analgesia (corresponds to MRI 4 in figure 1d). There is further progression of the recurrence in the presacral area and along the left sciatic nerve.

FIG. 4A
FIG. 4B
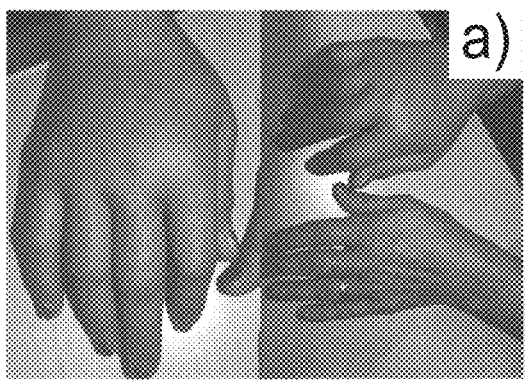
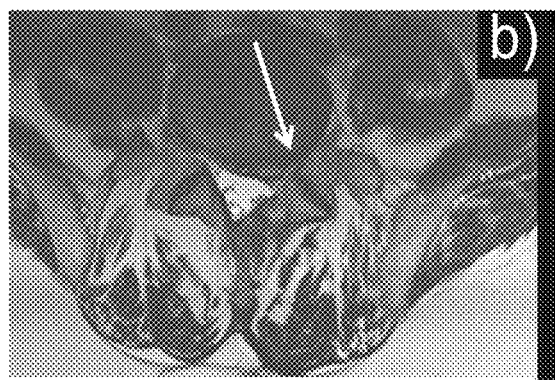
FIG. 4C
FIG. 4D

EGFR TARGETED THERAPY OF NEUROLOGICAL DISORDERS AND PAIN

CROSS REFERENCE TO RELATED APPLICATIONS

This application is a continuation of U.S. patent application Ser. No. 15/270,525, filed Sep. 20, 2016, allowed as U.S. Pat. No. 10,611,844, which is continuation of U.S. patent application Ser. No. 14/654,180, filed Jun. 19, 2015, which is a U.S. 371 National Phase Entry of International Patent Application No. PCT/EP2013/003931, filed Dec. 20, 2013, which claims the benefit of U.S. Provisional Patent Application No. 61/740,876, filed Dec. 21, 2012, the contents of which are incorporated by reference in their entireties.

FIELD OF THE INVENTION

The present invention relates to compositions and methods for treatment of neurological disorders. In particular, the present invention relates to the epidermal growth factor receptor (EGFR) as a clinical target for treatment of neurological disorders, preferably in conjunction with neuropathic pain. The invention relates in more detail to compositions comprising inhibitors of EGFR.

BACKGROUND OF THE INVENTION

Chronic and/or neuropathic pain after nerve injury is a major health problem worldwide. Neuropathic pain (NP) is caused by a primary lesion or disease of the somatosensory system (Jensen T S, Baron R, Haanpaa M, et al. A new definition of neuropathic pain. Pain 2011; 152:2204-5). Not uncommonly, its severity, chronicity and the poor side-effect to benefit ratio of current pharmacotherapy for NP (Dworkin R H. An overview of neuropathic pain: syndromes, symptoms, signs, and several mechanisms. Clin J Pain 2002; 18:343-9; Finnerup N B, Sindrup S H, Jensen T S. The evidence for pharmacological treatment of neuropathic pain. Pain 2010; 150:573-81) lead to severely impaired physical and psychological functioning among sufferers (Jensen M P, Chodroff M J, Dworkin R H. The impact of neuropathic pain on health-related quality of life: review and implications. Neurology 2007; 68:1178-82). In the general population, the incidence of NP is estimated to be 1% (Dieleman J P, Kerklaan J, Huygen F J, Bouma P A, Sturkenboom M C. Incidence rates and treatment of neuropathic pain conditions in the general population. Pain 2008; 137:681-8) and rising (Dworkin, supra). The resulting prevalence of moderate to severe chronic NP is 5% (Bouhassira D, Lanteri-Minet M, Attal N, Laurent B, Touboul C. Prevalence of chronic pain with neuropathic characteristics in the general population. Pain 2008; 136:380-7), making it a common and formidable health problem worldwide.

Despite the numerous etiologies of NP, the mechanism of its perpetuation, regardless of origin, appears to involve the interaction of neuronal, glial and immune cells (Scholz J, Woolf C J. The neuropathic pain triad: neurons, immune cells and glia. Nat Neurosci 2007; 10:1361-8). Communication between these cells has been attributed to signaling via the family of mitogen-activated protein kinase (MAPK) proteins (Ji R R, Gereau R Wt, Malcangio M, Strichartz G R. MAP kinase and pain. Brain Res Rev 2009; 60:135-48).

Neuropathic pain is a complex, chronic pain state that usually is accompanied by tissue injury. With neuropathic pain, the nerve fibers themselves may be damaged, dysfunctional or injured. These damaged nerve fibers send incorrect signals to other pain centers. The impact of nerve fiber injury includes a change in nerve function both at the site of injury and areas around the injury. Some neuropathic pain studies suggest the use of non-steroidal anti-inflammatory drugs, such as Aleve or Motrin, may ease pain. Some people may require a stronger painkiller, such as those containing morphine. Anticonvulsant and antidepressant drugs seem to work in some cases. If another condition, such as diabetes, is involved, better management of that disorder may alleviate the pain.

In cases that are difficult to treat, a pain specialist may use invasive or implantable device therapies to manage the pain. Electrical stimulation of the nerves involved in neuropathic pain generation may also control the pain symptoms.

Unfortunately, neuropathic pain often responds poorly to standard pain treatments and occasionally may get worse instead of better over time. For some people, it can lead to serious disability. Current treatments are characterized by an unsatisfactory side effect to benefit-ratio.

Thus, additional therapies that target neurological disorders such as neuropathic pain are urgently needed.

SUMMARY OF THE INVENTION

The present invention relates to compositions and methods for treatment of neurological disorders. In particular, the present invention relates to EGFR as a clinical target for treatment of neurological disorders, preferably accompanied by neuropathic pain.

EGFR is widely expressed on nerve fibers (Andres et al., Quantitative automated microscopy (QuAM) elucidates growth factor specific signalling in pain sensitization, Molceular Pain 2010, 6:98). However, in contrast to our observations, have several authors reported that EGFR inhibitors induced abdominal, chest and generalized pain when used in cancer therapy (Andres et al.: Quantitative automated microscopy (QuAM) elucidates growth factor specific signalling in pain sensitization, Molceular Pain 2010, 6:98.; Ciardiello et al., Interaction between the epidermal growth factor receptor (EGFR) and the vascular endothelial growth factor (VEGF) pathways: a rational approach for multi-target anticancer therapy. Ann Oncol 2006, 17(Suppl 7):vii109-114; Dragnev et al., Bexarotene and erlotinib for aerodigestive tract cancer. J Clin Oncol 2005, 23:8757-8764; Folprecht et al: Phase I pharmacokinetic/pharmacodynamic study of EKB-569, an irreversible inhibitor of the epidermal growth factor receptor tyrosine kinase, in combination with irinotecan, 5-fluorouracil, and leucovorin (FOLFIRI) in first-line treatment of patients with metastatic colorectal cancer. Clin Cancer Res 2008,14:215-223; and Atalay et al., Novel therapeutic strategies targeting the epidermal growth factor receptor (EGFR) family and its downstream effectors in breast cancer. Ann Oncol 2003, 14:1346-1363).

Surprisingly, and in contrast to these observations that EGFR inhibitors cause pain, the inventors have discovered that the administration of antigen binding protein EGFR inhibitors such as anti-EGFR antibodies like cetuximab (Erbitux®) and panitumumab (Vectibix®) or small molecule EGFR inhibitors such as gefitinib (Iressa®) and erlotinib (Tarceva®) alleviate symptoms across a range of various categories of neuropathic pain (e.g., toxic, metabolic, trauma, compressive, autoimmune, infectious and hereditary/congenital neuropathic pain) involving different types of nerve fibers. The effect can be observed even in cases where said inhibitors, which are per se known and approved as anti-cancer drugs, are applied to patients that do not suffer from cancer diseases.

Accordingly, the present invention provides for the use of EGFR inhibitors to treat pain symptoms in a subject. In some preferred embodiments, the present invention provides for the use of EGFR inhibitors to alleviate one or more symptoms of neuropathic pain in a subject. The present invention is not limited to alleviation of any particular symptoms of neuropathic pains and includes, but is not limited to alleviation of shooting and burning pain and well as tingling and numbness and combinations thereof.

Accordingly, in some embodiments, the present invention provides methods of treating a subject with pain, preferably neuropathic pain, more preferably severe neuropathic pain comprising administering to said subject an agent that inhibits at least one biological function of EGFR. The invention further provides compositions comprising at least an agent that inhibits at least one biological function of EGFR for use for the treatment of neurological disorders, preferably neurological disorders accompanied by pain, preferably severe neuropathic pain.

In some embodiments, the neuropathic pain is non-compressive neuropathic pain.

In some embodiments, the neuropathic pain is compressive neuropathic pain. In some embodiments, the compressive neuropathic pain is non-cancer related. In some embodiments, the compressive neuropathic pain is cancer related. In some embodiments, the compressive neuropathic pain is pain associated with a syndrome selected from the group consisting of failed back surgery syndrome, carpal tunnel syndrome, compartment syndrome and sciatica.

In some embodiments, the neuropathic pain is toxic neuropathic pain. In some embodiments, the toxic neuropathic pain is chemotherapy-induced peripheral neuropathy. In some embodiments, the toxic neuropathic pain is selected from pain associated with exposure to an agent selected from the group consisting of lead, arsenic, asbestos, isoniazid and thallium.

In some embodiments, the neuropathic pain is metabolic neuropathic pain. In some embodiments, the metabolic neuropathic pain is selected from pain associated with painful diabetic neuropathy, nutritional deficiency, alcohol induced neuropathy and thiamine deficient axonal sensorimotor burning neuropathy.

In some embodiments, the neuropathic pain is traumatic neuropathic pain. In some embodiments, the traumatic neuropathic pain is associated with a syndrome selected from the group consisting of phantom limb syndrome and complex regional pain syndrome.

In some embodiments, the neuropathic pain is autoimmune neuropathic pain. In some embodiments, the autoimmune neuropathic pain is selected from the group consisting of chronic inflammatory demyelinating polyneuropathy and vasculitic neuropathy.

In some embodiments, the neuropathic pain is infectious neuropathic pain. In some embodiments, the infectious neuropathic pain is selected from the group consisting of postherpetic neuralgia and painful HIV-distal sensory polyneuropathy. In some embodiments, the neuropathic pain is congenital or hereditary neuropathic pain.

In some embodiments, the pain is associated with pain nerve fiber type A. In some embodiments, the pain is associated with pain nerve fiber type B. In some embodiments, the pain is associated with pain nerve fiber type C. In some embodiments, the pain is associated with demyelinated nerve fibers.

In some embodiments, the agent reduces or modulates symptoms of said pain, wherein said symptom is selected from the group consisting of shooting pain, burning pain, tingling, numbness and combinations thereof.

In some embodiments, the method provides for the long term palliative care of a subject. In some embodiments, the long term palliative care is for a period selected from the group consisting of longer than six months, longer than 12 months, longer than 24 months, longer than 36 months, longer than 48 months and longer than 60 months.

In some embodiments, the method provides for reduction of the dosage of opioid agents for a subject. In some embodiments, the dosage of said agent is reduced following initial administration of said agent.

In some embodiments, the agent is an antigen binding protein that inhibits at least one biological function of EGFR, such as an anti EGFR antibody or a biologically effective fragment thereof. In some embodiments, the antigen binding protein is an anti EGFR antibody, selected from the group consisting of cetuximab, matuzumab, necitumumab, nimotuzumab, panitumumab, and zalutumumab. In some embodiments, the antigen binding protein is selected from the group consisting of cetuximab or panitumumab.

In some embodiments, the antigen binding protein is cetuximab and the administration is every 5 to 14 days. In some embodiments, the cetuximab is administered at an initial dose of about 300 to 500 mg per square meter, followed by weekly infusion of about 100 to 500 mg per square meter. In some embodiments, the antigen binding protein is panitumumab and the administration is every 10 to 20 days.

In some embodiments, the panitumumab is administered at an initial dose of 6 mg/kg, followed by biweekly infusions of about 6 mg/kg. In some embodiments, administration comprises infusion of an antigen binding protein inhibitor of EGFR.

In some embodiments, the agent is a small molecule drug that inhibits at least one biological function of EGFR, and said administration is oral. In some embodiments, the small molecule drug is selected from the group consisting of afatinib, erlotinib, gefitinib, lapatinib, and neratinib.

In some embodiments, the small molecule drug is selected from the group consisting of gefitinib and erlotinib. In some embodiments, the small molecule drug is gefitinib and the administration is 10 to 250 mg daily. In some embodiments, the small molecule drug is erlotinib and the administration is 10 to 300 mg daily. In some embodiments, the administration comprises oral administration of a small molecule inhibitor of EGFR.

In some embodiments, administration comprises administration of an antigen binding protein inhibitor of EGFR followed by administration of a small molecule inhibitor of EGFR. In some embodiments, the subject is a human.

In some embodiments, the present invention provides methods of treating a subject with a neurological disorder, preferably accompanied by neuropathic pain, comprising administering to said subject an agent that inhibits at least one biological function of an EGFR polypeptide. In some embodiments, the present invention provides pharmaceutical compositions comprising at least an agent that inhibits at least one biological function of an EGFR polypeptide for use for said treatment methods.

In some embodiments, the subject exhibits symptoms of a neurological disorder and said administering said agent reduces or modulates symptoms of said neurological disorder, preferably reduces or eliminates neuropathic pain In some embodiments, the subject does not have cancer or has not been previously treated for cancer. In a preferred embodiment of the invention, the neurological disorder is neuropathic pain, or is accompanied by neuropathic pain.

In some embodiments, the neurological disorder is selected from the group consisting of pain, sciatica, multiple sclerosis, depression, dementia, Parkinson's disease, stroke, axotomia, and ischemia or reperfusion injury, Down's syndrome and autism.

In some embodiments, the agent that inhibits at least one biological function of an EGFR polypeptide is co-administered with at least additional therapeutic agent, preferably a therapeutic agent that palliates or prevents pain In some embodiments, the at least additional therapeutic agent is selected from the group consisting of non-steroidal anti-inflammatory drugs, steroidal anti-inflammatory drugs, opioid-based drugs, antidepressants, anticonvulsants, antiepileptics, anti-anxiety drugs, and cannabinoids and combinations thereof.

The known agents according to the invention that inhibit at least one biological function of an EGFR polypeptide are currently used and approved as anti-cancer agents usually in a combination treatment with chemotherapeutic agents, such has irinotecan, FOLFIRI, FOLFOX, paclitaxel and others. In many cases, the anti-cancer effect of these agents, above all when anti-EGFR antibodies are applied, is present only in conjunction with a chemotherapeutic and/or radiotherapeutic treatment setting. In contrast to that, the agents and compositions according to the present invention elicit their pain-palliating efficacy independent on any anti-cancer efficacy, and independent on the presence of a cancer disease. Nonetheless, the EGFR inhibiting agents and compositions according to the invention, preferably cetuximab, panitumumab, erlotinib and gefitinib, can be successfully used as monotherapy in cancer therapy accompanied by neuropathic pain which is usually caused there by tumor growth and/or by the side effects of the applied chemotherapeutic agents. They are also effective in patients suffering from cancer and, in addition, from neurological diseases which are not caused or influenced by the primary or secondary cancer disease.

It is a striking result of the current invention that the EGFR inhibiting agents and compositions according to the invention, are effective in neuropathic pain reduction much faster than the same agents applied in a very similar dose setting in cancer therapy. If applied by intravenous administration by a one-time or initial dose of 250-500 mg/m$^2$ a pain reduction of at least 50% compared to the untreated condition can be obtained after less than 24 h, preferably less than 12 h, and most preferably less than 6 h.

Therefore, it is an object of the present invention to provide EGFR inhibiting agents according to the invention that reduce neuropathic pain in a patient suffering from a neurological disease and/or a cancer disease by intravenous administration of an initial or single dose of preferably 250-500 mg/m$^2$ of an antibody or polypeptide, such as cetuximab or panitumumab, and of 10-300 mg of a small molecule drug, such as erlotinib or gefitinib, by more than 50% of the individual pain score compared to untreated condition within 4 h-6 h after administration, and by more than 90% within 12 h-24 h after administration dependent on the nature and severity of the neuropathic pain. In case of cetuximab a pain reduction of about 90% can be obtained already after 4-6 h after administration.

It is a further object of the present invention to provide EGFR inhibiting agents according to the invention that reduce neuropathic pain in a patient suffering from a neurological disease and/or a cancer disease by intravenous administration of an initial or single dose of 250-500 mg/m$^2$ of an antibody or polypeptide, such as cetuximab or panitumumab, wherein said analgesic effect is lasting more than 4 days, preferably 5-20 days, without a second or further dose of the same agent is needed to be administered. As a rule, the intravenous administration may be repeated in this case every 5-14 days, preferably every 10-20 days, dependent on the nature of the drug. During this time, the additional administration of analgesic drugs can be reduced or omitted. Therefore, in another embodiment of the treatment, the simultaneous administration of other analgesic drugs, or pain killers, such as opioids, can be reduced by at least 50%, 60%, 70%, 80%, 90% or 100%.

In addition, it is an object of the present invention to provide EGFR inhibiting agents according to the invention that reduce neuropathic pain in a patient suffering from a neurological disease and/or a cancer disease by oral administration of an initial or single dose of preferably 50-200 mg to a patient suffering from a neurological disease by more than 50% compared to the untreated condition within 12 h-24 h after administration, and by more than 90% within 24 h-48 h after administration. As a rule, the oral administration may be repeated in this case every 1-3 days, preferably every day, dependent on the nature of the drug. During this time, the additional administration of analgesic drugs can be reduced or omitted. Therefore, in another embodiment of the treatment, the simultaneous administration of other analgesic drugs, or pain killers, such as opioids, can be reduced by at least 50%, 60%, 70%, 80%, 90% or 100%.

In another embodiment of the invention the treatment comprises a first initial intravenous administration of an anti-EGFR antibody, such as cetuximab and panitumumab, or a biologically active fragment thereof, followed after 5-20 days by oral administration of a small molecule drug, such as erlotinib or gefitinib, every 1-3 days, and optionally reducing or omitting other analgesic drugs such as opioids.

It was further found by the inventors that the EGFR inhibiting agents of the invention may reduce pathologic symptoms accompanying the neuropathic pain, for example, edema and skin rash in autoimmune neuropathic related disorders, like vasculitis neuropathy.

In sum, the inventions provides:

A pharmaceutical composition or a method for use of the composition comprising an agent that inhibits at least one biological function of EGFR for use for treating a subject suffering from a neurological disease accompanied by pain, solely or in conjunction with a cancer disease, wherein said pain is neuropathic pain selected from the group consisting of non-compressive neuropathic pain, compressive neuropathic pain, toxic neuropathic pain, metabolic neuropathic pain, traumatic neuropathic pain, autoimmune neuropathic pain, infectious neuropathic pain, and congenital or hereditary neuropathic pain. In a specific embodiment of the invention the methods and compositions are for use in for a treatment of neuropathic pain, wherein the neuropathic pain is compressive neuropathic pain in conjunction with a cancer disease, or wherein the neuropathic pain is toxic neuropathic pain in conjunction with chemotherapy.

A respective pharmaceutical composition or a method for use of the composition, wherein the agent that inhibits at least one biological function of EGFR is an anti-EGFR antibody or a biologically active portion thereof, and/or a small molecule drug inhibiting EGFR. According to the invention the anti-EGFR antibody is selected from the group consisting of cetuximab, panitumumab, matuzumab, necitumumab, nimotuzumab, and zalutumumab, and the small molecule drug is selected from the group consisting of afatinib, erlotinib, gefitinib, lapatinib, and neratinib.

A respective pharmaceutical composition or a method for use of the composition, wherein the anti-EGFR antibody is applied by at least one initial preferably intravenous infusion administration of 300 to 500 mg/m$^2$, followed by one or more subsequent administrations of about 100 to 500 mg/m$^2$ every 5 to 20 days, preferably every 7-20 days, dependent on the pharmacokinetic nature of the antibody, wherein said administration causes pain relief by 50 to 100% compared to the untreated subject within less than 4-10 h, preferably less than 2 h after said administration for at least 5 to 20 days, preferably 5 to 10 days.

A respective pharmaceutical composition or a method for use of the composition, wherein the small molecule drug is applied by preferably oral administration of an initial dose of 50 to 300 mg followed by a subsequent dose of 10-200 mg every 1 to 3 days, preferably daily, wherein said administration causes pain relief by 50 to 100% compared to the untreated subject within less than 12-24 h after said administration for at least 2 to 5 days, dependent on the pharmacokinetic nature of the drug.

A respective pharmaceutical composition or a method for use of the composition, wherein said anti-EGFR antibody is applied by at least one initial intravenous infusion administration of 300 to 500 mg/m$^2$, after 5 to 20 days, preferably every 7-20 days, dependent on the pharmacokinetic nature of the antibody, followed by at least one subsequent oral administration of said small molecule drug of about 10 to 300 mg, preferably 50 to 200 mg, every 1 to 3 days, preferably daily, wherein said administration causes pain relief by 50 to 100% compared to the untreated subject within less than 4-10 h after said initial administration of said anti-EGFR antibody, and said pain relief is lasting during the treatment intervals indicated.

A respective pharmaceutical composition or a method for use of the composition, wherein the anti-EGFR antibody is cetuximab or panitumumab, and the small molecule drug is erlotinib or gefitinib.

A respective pharmaceutical composition or a method for use of the composition wherein said EGFR inhibiting agent or agents is or are co-administered with at least one analgesic drug, selected from the group consisting of non-steroidal anti-inflammatory drugs, steroidal anti-inflammatory drugs, paracetamol, COX-2 inhibitors, opioids and cannabinoids, flupirtine, specific agents such as pregabalin and gabapentin.

A respective pharmaceutical composition or a method for use of the composition wherein an analgesic drug is additionally administered in an amount which is reduced by 10-100%, preferably by 50-90% compared to the subject which is not treated with said EGFR inhibiting agent.

DESCRIPTION OF THE FIGURES AND TABLES

FIGS. 1a-d describe graphically the clinical course of case 1 over period of 69 months. Progression of the pelvic tumor in case 1 during this period is shown in the magnetic resonance image (MRI) in FIG. 2a-c.

FIGS. 2a-c. Recurrent and progressive rectal cancer. Arrows indicate tumor changes affecting the left sacral plexus and left sciatic nerve. 2a. MRI taken three months prior to starting capecitabine, oxaliplatin and cetuximab (corresponds to MRI 2 in FIG. 1a). There is a presacral recurrence that extends along the left sciatic nerve. 2b. MRI taken 4 months after starting capecitabine, oxaliplatin and cetuximab (corresponds to MRI 3 in FIG. 1b). Both the presacral recurrence and its extension along the sciatic nerve have increased in size. MRI taken eight months after starting cetuximab monotherapy for analgesia (corresponds to MRI 4 in FIG. 1d). There is further progression of the recurrence in the presacral area and along the left sciatic nerve.

FIG. 3 provides graphs of BPI-measurements before and after introduction of EGFR-inhibition for cases 2-5.

FIGS. 4a-d provide graphic depictions of patients treated according to the present invention. a) Case 2. Photographs depicting the persistence of abnormalities typical of CRPS1, in the patient's right hand. Treatment with the EGRF inhibitor cetuximab relieved her NP but did not influence the vasomotor pathology of the underlying condition. b) Case 3. MRI taken six weeks postoperatively, due to recurrence of NP back pain, after initial relief. The image demonstrates pathological scar tissue formation around the patient's fifth lumbar spinal nerve root. c and d) Case 4. Computed tomography scan of the patient's pelvis before c) and after d) EGFR-inhibition. In the interval between the scans, the patient was completely relieved of his NP despite a growing pelvic tumor which increasingly invaded sacral nerves.

Figure 5:
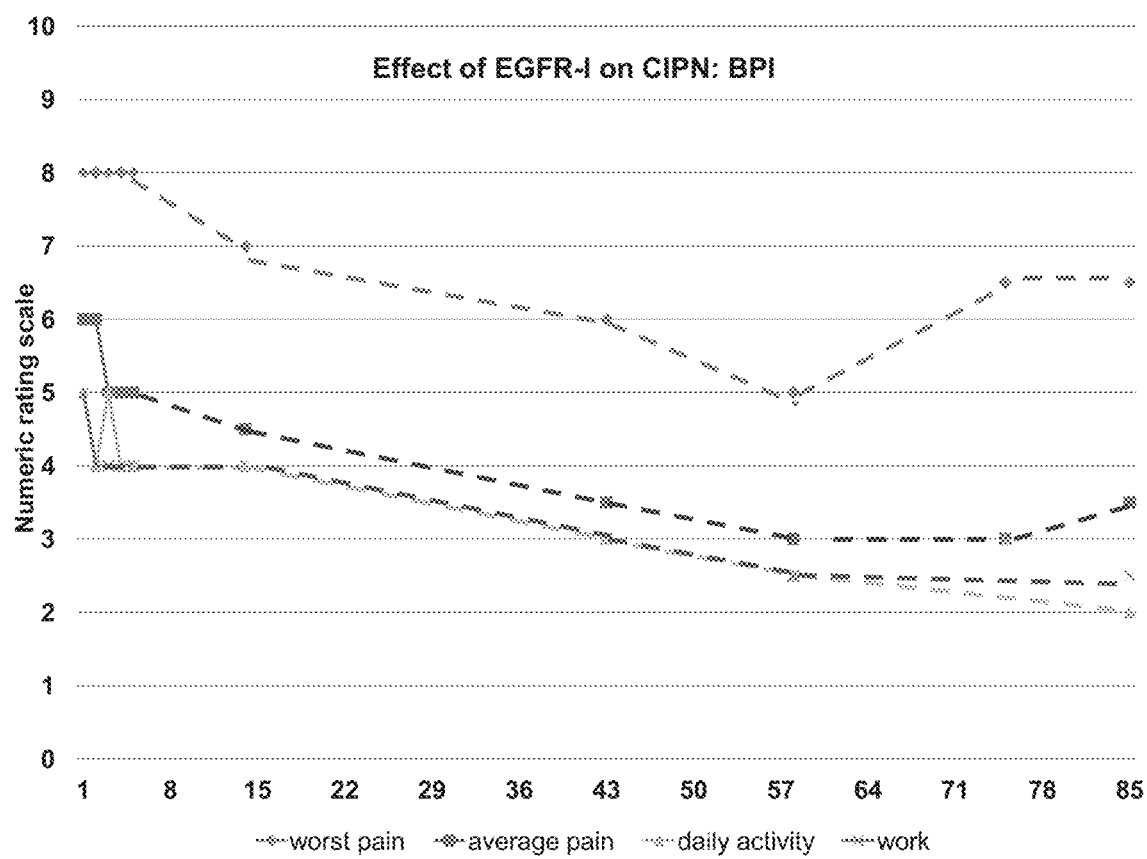

FIG. 5. Selected domains of the Brief Pain Inventory after starting intravenous EGFR-inhibition with panitumumab for progressive CIPN. Days since first treatment are shown on the X-axis (infusion repeated every 14 days).

Figure 6:
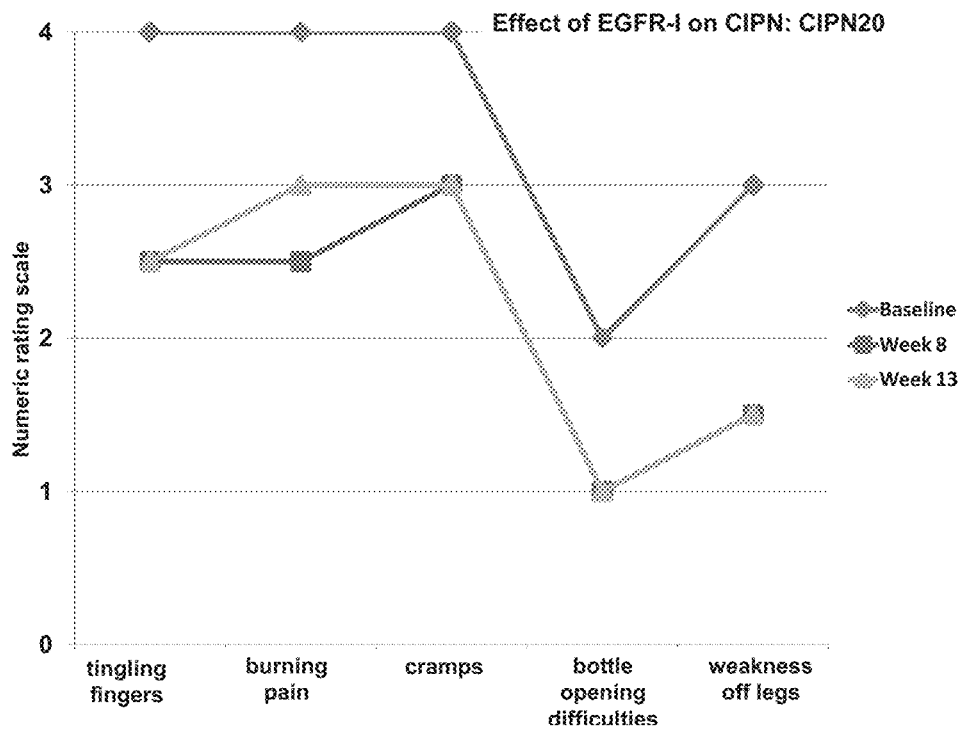

FIG. 6. Alleviation of CIPN by EGFR-I exemplified by selected questions from the EORTC QLQ-CIPN20. Five of the twenty questionnaire items are shown. None of the responses deteriorated after start of treatment (data not shown).

Figure 7:
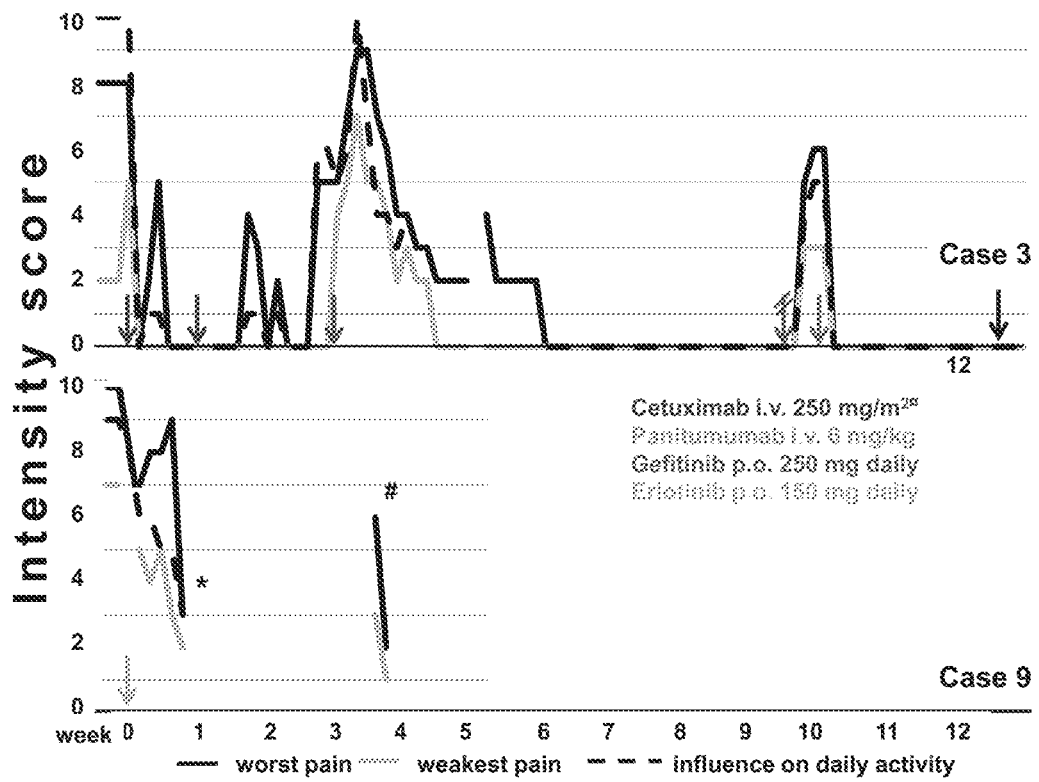

FIG. 7. Oral EGFR-I effective against NP according to BPI scores. The upper panel shows patient 3, who experienced recurrent severe NP after wash-out of the intravenous drug cetuximab. The pain was completely alleviated after two to three weeks of treatment with the oral EGFR-I gefitinib. The lower panel shows a previously EGFR-I naïve patient, who responded to upfront treatment with the oral EGFR-I erlotinib, yellow arrow.

DETAILED DESCRIPTION OF THE INVENTION

To facilitate an understanding of the present invention, a number of explanations, terms and phrases are given and defined below:

The epidermal growth factor receptor EGFR (synonyms: ErbB-1; HER1) is a member of the ErbB family of receptors, a subfamily of four closely related receptor tyrosine kinases: EGFR (ErbB-1), HER2/c-neu (ErbB-2), Her3 (ErbB-3) and Her4 (ErbB-4).

The EGF receptor is a transmembrane glycoprotein which has a molecular weight of 170,000, and is found on many epithelial cell types. It is activated by at least three ligands, EGF, TGF-α (transforming growth factor alpha) and amphiregulin. Both epidermal growth factor (EGF) and transforming growth factor-alpha (TGF-a) have been demonstrated to bind to EGF receptor and to lead to cellular proliferation and tumor growth.

Two important types of ErbB inhibitor are in clinical use: chimeric, humanized or fully human antibodies directed against the extracellular domain of EGFR or ErbB2, and small-molecule tyrosine-kinase inhibitors (TKIs) that compete with the ATP in the tyrosine-kinase domain of the receptor.

A number of murine and rat monoclonal antibodies against EGF receptor have been developed and tested for their ability inhibit the growth of tumor cells in vitro and in vivo (Modjtahedi and Dean, 1994, *J. Oncology* 4, 277).

Humanized monoclonal antibody 425 (hMAb 425, U.S. Pat. No. 5,558,864; EP 0531 472) and chimeric monoclonal antibody 225 (cMAb 225), both directed to the EGF receptor, have shown their efficacy in clinical trials. The C225 antibody (Cetuximab) was demonstrated to inhibit EGF-mediated tumor cell growth in vitro and to inhibit human tumor formation in vivo in nude mice. The antibody as well as in general all anti-EGFR antibodies act mostly in synergy with certain chemotherapeutic agents (i.e., doxorubicin, adriamycin, taxol, and cisplatin) to eradicate human tumors in vivo in xenograft mouse models (see, for example, EP 0667165). Ye et al. (1999, Oncogene 18, 731) have reported that human ovarian cancer cells can be treated successfully with a combination of both chimeric MAb 225 and humanized MAb 4D5 which is directed to the HER2 receptor. Besides anti-ErbB antibodies, there are numerous small chemical molecules which are known to be potent inhibitors of ErbB receptor molecules blocking the binding site of the natural ligands (see detailed description), or blocking the tyrosine residues of the binding site of the receptor kinase, thus preventing phosphorylation and further cascade signaling.

The term "tyrosine kinase antagonist/inhibitor" or "ErbB-inhibitor" refers according to this invention to natural or synthetic agents that are enabled to inhibit or block tyrosine kinases, receptor tyrosine kinases included. Thus, the term includes per se ErbB receptor antagonists/inhibitors, and specifically EGFR inhibitors.

With exception of the anti-ErbB receptor antibodies mentioned above and below, more preferable tyrosine kinase antagonist agents under this definition are chemical compounds which have shown efficacy in mono-drug therapy for breast and prostate cancer. Suitable indolocarbazole-type tyrosine kinase inhibitors can be obtained using information found in documents such as U.S. Pat. Nos. 5,516,771; 5,654,427; 5,461,146; 5,650,407; 5,475,110; 5,591,855; 5,594,009 and WO 96/11933 disclose pyrrolocarbazole-type tyrosine kinase inhibitors and prostate cancer. One of the most promising anti-cancer agents in this context is gefitinib (IRESSA®, Astra Zeneca), which is reported to possess outstanding therapeutic efficacy and excellent tolerability in patients with non-small cell lung cancer (NSCLC) as well as advanced head and neck cancer.

"Antibody fragments" comprise a portion of an intact antibody, preferably comprising the antigen-binding or variable region thereof. Examples of antibody fragments include Fab, Fab', F(ab')2, Fv and Fc fragments, diabodies, linear antibodies, single-chain antibody molecules; and multispecific antibodies formed from antibody fragment(s). An "intact" antibody is one which comprises an antigen-binding variable region as well as a light chain constant domain (CL) and heavy chain constant domains, CH1, CH2 and CH3.

As used herein, the term "inhibits at least one biological activity of EGFR" refers to any agent that decreases any activity of EGFR, including EGFR tyrosine kinase (e.g., including, but not limited to, the activities described herein), via directly contacting EGFR protein, contacting EGFR mRNA or genomic DNA, causing conformational changes of EGFR polypeptides, decreasing EGFR protein levels, or interfering with EGFR interactions with different receptors or ligands such as but not limited to EGF, TGF-alpha, Neuregulin, Amphiregulin, Epiregulin, NGF, HER2, HER3 and HER4. Inhibitors also include molecules that indirectly regulate EGFR biological activity by intercepting upstream signaling molecules. In other words, the invention is related to EGFR inhibitors that bind to the extracellaur binding site of the tyrosine kinase receptor molecule, thus blocking binding of the natural ligands, such as EGF. Antibodies, antibody portions, and peptides comprising epitopes that target this extracellular EGF receptor binding domain, are included by the invention. The invention is further related to EGFR inhibitors which can bind or interact with the intracellular phosphorylation site or domain of the tyrosine kinase receptor molecule, such preventing or decreasing phosphorylation by tyrosine kinase. This can be achieved by small (chemical) molecule drugs.

As used herein, the term "neuropathic pain" refers to a complex, chronic pain state that usually is accompanied by tissue injury. Neuropathic pain includes, but is not limited to, the following syndromes and disease states: nerve impingement, complex regional pain syndrome types I and II, trigeminal neuralgia, phantom pain, diabetic neuropathy, spinal cord injury, and nerve damage due to i.e. cancer, burns and trauma. Different categories of neuropathic pain include, but are not limited to, toxic, metabolic, trauma, compressive, autoimmune, infectious and hereditary/congenital neuropathic pain.

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" or "patient" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "in vitro" refers to an artificial environment and to processes or reactions that occur within an artificial environment. In vitro environments can consist of, but are not limited to, test tubes and cell culture.

The term "in vivo" refers to the natural environment (e.g., an animal or a cell) and to processes or reaction that occur within a natural environment. The term "pain interference (total) score" means a score for pain as a result of the disease occurring during administration of the effective drug. Pain interference is assessed using the Brief Pain Inventory (BPI). BPI is used to evaluate pain interference with the following: (a) general activity, (b) mood, (c) walking ability, (d) normal work, (e) relations with other people, (f) sleep, and (g) enjoyment of life. Total score for pain interference is calculated as: (Mean score of non-missing questions)×(7/number of non-missing questions). If four or more questions are missing, the pain interference total score is set to missing.

The term "chemotherapeutic agent" or "anti-neoplastic agent" is regarded according to the understanding of this invention as a member of the class of "cytotoxic agents", as specified above, and includes chemical agents that exert anti-neoplastic effects, i.e., prevent the development, maturation, or spread of neoplastic cells, directly on the tumor cell, and not indirectly through mechanisms such as biological response modification. Suitable chemotherapeutic agents according to the invention are preferably natural or synthetic chemical compounds, but biological molecules, such as proteins, polypeptides etc. are not expressively excluded. There are large numbers of anti-neoplastic agents available in commercial use, in clinical evaluation and in pre-clinical development, which could be included in the present invention for treatment of tumors/neoplasia by combination therapy with TNFα and the anti-angiogenic agents as cited above. It should be pointed out that the chemotherapeutic agents can be administered optionally together with above-said antibody drug. Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; cytotoxic antibiotics and camptothecin derivatives. Preferred chemotherapeutic agents or chemotherapy include amifostine (ethyol), cabazitaxel, cisplatin, dacarbazine (DTIC), dactinomycin, docetaxel, mechlorethamine, streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, ketoconazole, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof. Most preferred chemotherapeutic agents according to the invention in combination with Dl17E6 are cabazitaxel, cisplatin, docetaxel, gemcitabine, doxorubicin, paclitaxel (taxol), irinotecan and bleomycin.

The present invention relates to compositions and methods for treatment of neurological disorders. In particular, the present invention relates to EGFR as a clinical target for treatment of neurological disorders.

Pain is transmitted via different nerve fibers, designated Aδ nerve fibers, B nerve fibers and C nerve fibers. In general, pain signals travel from the periphery to the spinal cord along an A-delta or C fiber. Because the A-delta fiber is thicker than the C fiber, and is thinly sheathed in an electrically insulating material (myelin), it carries its signal faster (5-30 m/s) than the unmyelinated C fiber (0.5-2 m/s). Pain evoked by the (faster) A-delta fibers is described as sharp and is felt first. This is followed by a duller pain, often described as burning, carried by the C fibers.

Neuropathic pain is caused by damage or disease affecting any part of the nervous system involved in bodily feelings (the somatosensory system). Neuropathic pain is a complex, chronic pain state. With neuropathic pain, the nerve fibers themselves may be damaged, dysfunctional, or injured. These damaged nerve fibers send incorrect signals to other pain centers. The impact of nerve fiber injury includes a change in nerve function both at the site of injury and areas around the injury. Some common causes of neuropathic pain include: Alcoholism; Amputation; Back, leg, and hip problems; Chemotherapy; Diabetes; Facial nerve problems; HIV infection or AIDS; Multiple sclerosis; Shingles and Spine surgery. Symptoms of neuropathic pain include shooting and burning pain and well as tingling and numbness.

EGF-MAPK-signaling is activated in neurons and glial cells in response to injury or dysfunction. Inhibition of the EGFR may interrupt a negative feedback loop, thereby alleviating symptoms from neurological disorders, like pain, neuropathic pain, MS, depression, dementia, Parkinson's disease, stroke, axotomia, etc. Especially in neuropathic pain, the pathological sensitization of nerve fibers for pain is inhibited.

Pain due to nerve injury is thought to be generated and sustained by MAPK signalling via the three pathways ERK, p38 and JNK in central, spinal and peripheral nerves, as well as in peripheral and central glia such as astrocytes and Schwann cells (Ji R R, Gereau R Wt, Malcangio M, Strichartz G R. MAP kinase and pain. Brain Res Rev 2009; 60(1):135-48). Furthermore, communication between neuronal cells, glial cells and immune cells is an established pathogenic factor in neuropathic pain (Scholz J, Woolf C J. The neuropathic pain triad: neurons, immune cells and glia. Nat. Neurosci. 2007; 10(11):1361-8). Activation of and communication between these cells after nerve injury has been shown to be dependent on MAPK signalling, potentially activated by EGFR, which is upregulated in the nervous system (Werner M H, Nanney L B, Stoscheck C M, King L E. Localization of immunoreactive epidermal growth factor receptors in human nervous system. J. Histochem.

Cytochem. 1988; 36(1):81-6; Maklad A, Nicolai J R, Bichsel K J, Evenson J E, Lee T C, Threadgill D W, et al. The EGFR is required for proper innervation to the skin. J. Invest. Dermatol. 2009; 129(3):690-8; Ji R R. Mitogen-activated protein kinases as potential targets for pain killers. Curr Opin Investig Drugs 2004; 5M:71-5).

The activation of the MAPK-signaling pathways is of established importance in neurological diseases and neuropathic pain. EGFR-inhibition blocks several of these pathways effectively (JNK, RAS-MEK-ERK, STAT, etc). Embodiments of the present invention provide methods of treating neurological disorders by inhibiting EGFR. The present invention is not limited to a particular neurological disorder. For example, in some embodiments, the present invention provides methods of inhibiting the EGF receptor to treat pain, neuropathic pain, MS, depression, dementia, Parkinson's disease, stroke, ischemia and reperfusion injury, ischemic brain injury, and axotomia. See e.g., Oyagi et al., Neuroscience. 2011 Jun. 30; 185:116-24 and Chen-Plotikin et al., Ann Neurol. 2011 April; 69(4):655-63. It is also contemplated that administration of the agents of the present invention is useful for ameliorating symptoms associated with genetics disorders such as Down's syndrome and autism.

Accordingly, the present invention provides methods of utilizing a reagent that inhibits at least one biological function of an EGFR polypeptide to reduce, ameliorate or modulate, or provide prophylaxis, for one or more symptoms associated with the following diseases or disorders: pain, neuropathic pain, sciatica, MS, depression, dementia, Parkinson's disease, stroke, ischemia and reperfusion injury, ischemic brain injury, axotomia, Amyotrophic lateral sclerosis, Huntington's disease, Chorea, Down's syndrome and autism.

In particularly preferred embodiments, the present invention provides novel treatment for neuropathic pain. The present invention is not limited to treatment of any particular type of neuropathic pain, and includes, but is not limited to treatment of the following types of neuropathic pain.

Ischemic NP—This category includes neuropathic pain associated with stroke, gangrene, and other peripheral thrombotic events.

Toxic NP—The most common toxic condition causing neuropathic pain is a result of chemotherapy and/or radiation in the treatment of cancer. Isoniazid and thallium are also known to cause neuropathic pain conditions. Exposure to chemicals like lead and arsenic also result in nerve damage. Toxic exposure generally results in abnormalities in genetic/protein processing.

Metabolic NP—Diabetes is clearly the major cause of neuropathic pain (e.g., painful diabetic neuropathy) caused by metabolic dysfunction. Nutritional deficiencies like Beriberi (vitamin B1) also produce neuropathic pain. In the case of diabetes, glycosylation end products inhibit axonal transport and Na+/K+ ATPase producing axonal degeneration. Alcohol induced neuropathy is often a result of thiamine (B1) deficiency although it can produce its own small fiber pain pathology as opposed to a thiamine-deficient axonal sensorimotor burning neuropathy.

Trauma NP—Typically trauma is due to fractures, direct nerve damages and burns. Trauma can also result in phantom limb syndromes and/or complex regional pain syndromes (CRPS). Phantom limb pain is thought to be a result of abrupt loss of sensory input from the peripheral limb to the brain and discharges from the nerve endings at the sight of the amputation that continue to send pain signals to the brain, making the brain think the limb is still there. There is no known mechanism that causes CRPS but many hypotheses have been suggested, including dysfunctional processing throughout the entire nervous system involving peripheral, central and autonomic neurons.

Compressive NP—Both nerve entrapment and excessive external pressure on nerve axons can cause ischemic or distortional (stretching) changes. Prolonged injury results in Wallerian degeneration of the axon with resultant muscle atrophy. Carpal tunnel syndrome and compartment syndromes are common entrapment injuries. The present invention also encompasses treatment of sciatica and trigeminal neuropathic pain.

Autoimmune NP—This class of neuropathic pain can be quite diverse. They may have autoimmune antibodies involved in their pathophysiology and are usually amenable to immune therapy. Some examples of autoimmune neuropathic pain include chronic inflammatory demyelinating polyneuropathy (CIDP), paraneoplastic syndromes and vasculitic neuropathy.

Infectious NP—Viral conditions are known to result in long-standing neuropathic pain. The classical condition is post-herpetic neuralgia caused by reactivation of the Varicella Zoster Virus. Lyme Disease (spirochetes), Chagas' Disease (trypanosomes), leprosy (mycobacterium), HIV, and Guillain-Barré Syndrome (post-infectious) can all cause neuropathic pain. The present invention specially encompasses treatment of postherpetic neuralgia and painful HIV-distal sensory polyneuropathy as well as neuropathic pain caused by the agents described above.

Congenital/Hereditary NP—Fabry's Disease and Charcot-Marie-Tooth Disease (burning pain in extremities) are examples of peripheral neuropathic pain associated with congenital abnormalities. Other hereditary conditions like amyloidosis also produce painful conditions.

Accordingly, in some embodiments, the present invention provides methods of treating a subject with pain comprising administering to said subject an agent that inhibits at least one biological function of EGFR. In some embodiments, the pain is neuropathic pain. In some embodiments, administration of an EGFR inhibitor causes alleviation of pain symptoms or a reduction in pain symptoms. The present invention is not limited to alleviation of any particular symptoms of neuropathic pain and includes, but is not limited to alleviation or reduction of shooting and burning pain and well as tingling and numbness and combinations thereof.

The neuropathic pain may be non-compressive neuropathic pain or compressive neuropathic pain. The compressive neuropathic pain can be cancer related or non-cancer related. In some embodiments, the compressive neuropathic pain is pain associated with a syndrome selected from the group consisting of failed back surgery syndrome, failed back surgery syndrome, carpal tunnel syndrome, compartment syndrome and sciatica, although treatment of other syndromes associated with compressive neuropathic pain are encompassed by the invention.

The neuropathic pain may be toxic neuropathic pain. In some embodiments, the toxic neuropathic pain is chemotherapy-induced peripheral neuropathy. In some embodiments, the neuropathic pain is selected from pain associated with exposure to an agent selected from the group consisting of lead, arsenic, asbestos, isoniazid and thallium. Other types of toxic neuropathic pain are also encompassed by the invention.

The neuropathic pain may be metabolic neuropathic pain. In some embodiments, the metabolic neuropathic pain is selected from pain associated with painful diabetic neuropathy, nutritional deficiency, alcohol induced neuropathy and thiamine deficient axonal sensorimotor burning neuropathy. Other types of metabolic neuropathic pain are also encompassed by the invention.

The neuropathic pain may be trauma neuropathic pain. In some embodiments, the trauma neuropathic pain is associated with a syndrome selected from the group consisting of phantom limb syndrome and complex regional pain syndrome. Other types of trauma neuropathic pain are also encompassed by the invention.

The neuropathic pain may be autoimmune neuropathic pain. In some embodiments, the autoimmune neuropathic pain is selected from the group consisting of chronic inflammatory demyelinating polyneuropathy and vasculitic neuropathy. Other types of autoimmune neuropathic pain are also encompassed by the invention.

The neuropathic pain may be infectious neuropathic pain. In some embodiments, the infectious neuropathic pain is selected from the group consisting of postherpetic neuralgia and painful HIV-distal sensory polyneuropathy. Other types of infectious neuropathic pain are also encompassed by the invention.

The neuropathic pain may be or hereditary neuropathic pain. In some embodiments, the neuropathic pain is associated with Fabry's Disease and Charcot-Marie-Tooth Disease. Other types of hereditary/congenital neuropathic pain are also encompassed by the invention.

The present invention likewise applies to treatment of pain associated with different types of nerve fibers. In some embodiments, the pain is associated with pain nerve fiber type A, nerve fiber type B, nerve fiber type C, demyelinated nerve fibers or combinations thereof.

In some embodiments, the present invention provides for the long term palliative care of a subject. In some embodiments, the long term palliative care is for a period selected from the group consisting of longer than six months, longer than 12 months, longer than 24 months, longer than 36 months, longer than 48 months and longer than 60 months and up to about 10 years or longer. In some embodiments, the present invention provides for reduction of the dosage of opioid agents or addictive pain relievers for a subject, or indeed, the need to administer opioid or other addictive pain relievers to a subject. In some embodiments, the dosage of the EGFR inhibitor is reduced following initial administration of said agent.

Antibody Therapy

In some embodiments, the present invention utilizes antibodies that target EGFR. Any suitable antibody (e.g., monoclonal, polyclonal, or synthetic) may be utilized in the therapeutic methods disclosed herein.

In some embodiments, neurological disorders such as neuropathic pain are treated with an antigen binding protein. Suitable antigen binding proteins include, but are not limited to, cetuximab, matuzumab, necitumumab, nimotuzumab, panitumumab, and zalutumumab. In some preferred embodiments, the monoclonal antibody cetuximab (commercialized by Eli Lilly, USA, and Merck KGaA, Germany) is used.

Cetuximab is a recombinant chimeric IgG1 antibody that binds to the extra-cellular domain of epidermal growth factor receptor with a higher affinity than either endogenous ligand. This binding inhibits receptor phosphorylation and activation and it leads to receptor internalization and degradation. (The biological properties of cetuximab. Vincenzi B, Schiavon G, Silletta M, Santini D, Tonini G. Crit Rev Oncol Hematol. 2008 November; 68(2):93-106. Epub 2008 Aug. 3. Review). Cetuximab is licensed to treat cancer, and is approved in colorectal cancer without K-RAS mutation in the EGF-signalling pathway. Cetuximab was developed to inhibit EGFR-activation, leading to the further inhibition of several pathways, among others, MAPK-signalling. This IgG1 antibody is used in colorectal cancer to inhibit the activation by the ligand EGF, but since it blocks the EGFR it inhibits binding of other EGF-binding ligands as well.

Erbitux is currently approved for the treatment of patients with epidermal-growth-factor-receptor (EGFR)-expressing, KRAS wild-type metastatic colorectal cancer:
   in combination with irinotecan-based chemotherapy;
   in first-line in combination with FOLFOX;
   as a single agent in patients who have failed oxaliplatin- and irinotecan-based therapy and who are intolerant to irinotecan.
      Erbitux is indicated for the treatment of patients with squamous cell cancer of the head and neck:
   in combination with radiation therapy for locally advanced disease;
   in combination with platinum-based chemotherapy for recurrent and/or metastatic disease.

Cetuximab (Erbitux®) is administered according to the invention by infusion into the subject or patient. In some preferred embodiments, cetuximab is administered every 5 to 14 days, most preferably about every 7 days. In some embodiments, cetuximab is administered at an initial dose of about 300 to 500 mg per square meter, most preferably about 400 mg per square meter, followed by weekly infusions of about 100 to 500 mg per square meter, preferably about 250 mg per square meter. The dose and the dose regimen of cetuximab according to the invention is similar to the treatment of cancer. Currently, there is a tendency that the doses can be slightly reduced by 10-30% compared to the cancer therapy, without affecting the anti-pain efficacy. Ongoing trials have to verify these results.

In other preferred embodiments, the monoclonal antibody panitumumab is utilized (Amgen, Thousand Oaks, Calif.).

Panitumumab is a fully human monoclonal antibody specific to the epidermal growth factor receptor (also known as EGF receptor, EGFR, ErbB-1 and HER1 in humans). Panitumumab was approved by the European Medicines Agency (EMEA) in 2007, and by Health Canada in 2008 for "the treatment of refractory EGFR-expressing metastatic colorectal cancer in patients with non-mutated (wild-type) KRAS.

The recommended dose of panitumumab (Vectibix®) is 6 mg per kilogram body weight given once every two weeks as an infusion. The recommended infusion time is around 60 minutes, but larger doses may need 90 minutes. The dose may need to be modified if severe skin reactions occur.

According to the invention panitumumab is administered every 10 to 20 days, most preferably about every 14 days. In some embodiments, panitumumab is administered at an initial dose of 6 mg/kg mg per square meter, followed by bi-weekly infusions of 6 mg/kg In some embodiments, infusion therapy with antigen binding proteins is combined with administration of small molecule EGFR inhibitors, which are described in more detail below. In some embodiments, the subjects are first treated with the antigen binding protein for a period of from about 1 to about 2, 3, 4, 5, 6, 7, 8, 9, or 10 weeks and then switched to treatment with the small molecule EGFR inhibitor which may preferably be administered orally.

In preferred embodiments, antibody based therapeutics are formulated as pharmaceutical compositions as described below. In preferred embodiments, administration of an antibody composition of the present invention results in a measurable decrease in symptoms of a neurological disorder.

Small Molecule Therapy

Some embodiments of the present invention utilize small molecules that inhibit one or more biological activities of EGFR. Small molecule therapeutics are identified, for example, using the drug screening methods described herein. In some embodiments, the small molecule therapeutics useful in the present invention include, but are not limited to, afatinib, erlotinib, gefitinib, lapatinib, neratinib and vandetanib. In some preferred embodiments, the small molecule is gefitinib or erlotinib, tradenamed Iressa (AstraZeneca, London, UK) and Tarceva (Genentech, South San Fransisco, Calif.), respectively (Activation of epidermal growth factor receptors in astrocytes: from development to neural injury. Liu B, Neufeld A H. J Neurosci Res. 2007 December; 85(16):3523-9. Review).

In some embodiments, the present invention provides for the oral administration of a small molecule EGFR inhibitor to reduce or alleviate one or more symptoms of neuropathic pain. In some embodiments, the present invention provides therapeutic regimes where a small molecule EGFR inhibitor is administered either before, or more preferably after, administration of antigen binding protein EGFR inhibitor. In some embodiments, the small molecule EGFR inhibitor is administered beginning from about 7 to 14 days following infusion of an antigen binding protein EGFR inhibitor. In some preferred embodiments, the small molecule drug is gefitinib and said administration is 10 to 250 mg daily. In other preferred embodiments, the small molecule drug is erlotinib and said administration is 10 to 300 mg daily.

Pharmaceutical Compositions

The present invention further provides pharmaceutical compositions (e.g., comprising pharmaceutical agents that modulate the expression or activity of EGFR) for use in the methods described above. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention also include, but are not limited to, solutions, emulsions, and liposome-containing formulations. These compositions may be generated from a variety of components that include, but are not limited to, preformed liquids, self-emulsifying solids and self-emulsifying semisolids. Pharmaceutical compositions of the present invention further include nanoparticle compositions such as inorganic nanoparticles, polymeric nanoparticles, solid lipid nanoparticles, liposomes, nanocrystals, nanotubes and dendrimeric particles.

The pharmaceutical formulations of the present invention, which may conveniently be presented in unit dosage form, may be prepared according to conventional techniques well known in the pharmaceutical industry. Such techniques include the step of bringing into association the active pharmaceutical agent with the pharmaceutical carrier(s) or excipient(s). In general the formulations are prepared by uniformly and intimately bringing into association the active ingredients with liquid carriers or finely divided solid carriers or both, and then, if necessary, shaping the product.

The pharmaceutical compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual agents, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the agent is administered in maintenance doses, ranging from 0.01 µg to 100 g per kg of body weight, once or more daily, to once every 20 years.

Combination Therapy

The EGFR inhibitors of the invention may be combined with other therapeutic drugs which may support the therapy of the subject's neurological disorder and neuropathic pain with the EGFR inhibitors of the invention, optionally by allowing a lower dose of the EGFR-inhibitor of the invention. Therefore, in some embodiments, the present invention provides therapeutic methods comprising one or more compositions described herein (e.g., EGFR inhibitors) in combination with an additional agent (e.g., an agent for treating neurological disorders or neuropathic pain). The present invention is not limited to a particular agent. Examples include, but are not limited to: anti-inflammatory agents such as NSAIDs and steroids; opioid pain killers; antidepressants such as tricyclics and serotonin-norepinephrine reuptake inhibitors (SNRIs); anticonvulsants such as gabapentin; antiepileptics; benzodiazapines; anti-anxiety drugs such as selective serotonin reuptake inhibitors (SSRIs); dietary supplements such as alpha lipoic acid and benfotiamine; cannabinoids; and the like.

Classes of useful agents for combination therapy include, for example, non-steroidal anti-inflammatory drugs (NSAIDS) such as Aspirin (Anacin, Ascriptin, Bayer, Bufferin, Ecotrin, Excedrin), Choline and magnesium salicylates (CMT, Tricosal, Trilisate), Choline salicylate (Arthropan), Celecoxib (Celebrex), Diclofenac potassium (Cataflam), Diclofenac sodium (Voltaren, Voltaren XR), Diclofenac sodium with misoprostol (Arthrotec), Diflunisal (Dolobid), Etodolac (Lodine, Lodine XL), Fenoprofen calcium (Nalfon), Flurbiprofen (Ansaid), Ibuprofen (Advil, Motrin, Motrin IB, Nuprin), Indomethacin (Indocin, Indocin SR), Ketoprofen (Actron, Orudis, Orudis KT, Oruvail), Magnesium salicylate (Arthritab, Bayer Select, Doan's Pills, Magan, Mobidin, Mobogesic), Meclofenamate sodium (Meclomen), Mefenamic acid (Ponstel), Meloxicam (Mobic), Nabumetone (Relafen), Naproxen (Naprosyn, Naprelan), Naproxen sodium (Aleve, Anaprox), Oxaprozin (Daypro), Piroxicam (Feldene), Rofecoxib (Vioxx), Salsalate (Amigesic, Anaflex 750, Disalcid, Marthritic, Mono-Gesic, Salflex, Salsitab), Sodium salicylate (various generics), Sulindac (Clinoril), Tolmetin sodium (Tolectin), Valdecoxib (Bextra); steroidal anti-inflammatory drugs including hydrocortisone, prednisone, methylprednisolone, beclomethasone, beclomethasone, budesonide, flunisolide, fluticasone propionate, triamcinolone and the like; and opiate-based pain killers including, but not limited to, fentanyl, hydromorphone, methadone, morphine, oxycodone, and oxymorphone; antidepressants, including tricyclic compounds such as bupropion, nortriptyline, desipramine, amitriptyline, amitriptylinoxide, butriptyline, clomipramine, demexiptiline, dibenzepin, dimetacrine, dosulepin/dothiepin, doxepin, imipramine, amineptine, iprindole, opipramol, tianeptine, trimipramine, imipraminoxide, lofepramine, melitracin, metapramine, nitroxazepine, noxiptiline, pipofezine, propizepine, protriptyine, and quinupramine and SNRIs such as duloxetine, venlafaxine, desvenlafaxine, milnacipran, levomilnacipran, sibutramine, bicifadine, and SEP-227162; anticonvulsants such as pregabalin, gabapentin, carbamazepine, and oxcarbazepine and benzodiazepines (e.g., alprazolam, bretazenil, bromazepam, brotizolam, chlordiazepoxide, cinolazepam, clonazepam, clorazepate, clotiazepam, cloxazolam, delorazepam, diazepam, estazolam, etizolam, flunitrazepam, flurazapam, flutoprazepam, halazepam, ketazolam, loprazolam, lorazepam, lormetazepam, medazepam, midazolam, nemetazepam, nitrazepam, nordazepam, oxazepam, phenazepam, pinazepaam, prazepam, premazepam, quazepam, temazepam, tetrazepam, triazolam, clobazam, DMCM, flumazenil, eszopiclone, zaleplon, zolpidem, and zopiclone); selective serotonin re-uptake inhibitors (SSRIs) such as citalopram, dapoxetine, escitalopram, fluoxetine, fluvoxamine, indalpin, paroxetine, sertraline, and zimelidine; and cannabinoids such as delta-9-tetrahydrocannabinol and nabilone.

The drugs and pharmaceutical compositions according to the inventions may be further co-administered or combined in conjunction with other drugs than analgesics as described above. For example, if the neuropathic pain is cancer related, the therapy may include co-administration with anti-cancer drugs or with drugs that reduce the side effect of said anti-cancer drugs or of chemotherapy or radiotherapy. So, it is possible to treat a cancer patient with an anti-cancer drugs and in concurrently or subsequently with the EGFR inhibitors according to the invention in order to treat the neuropathic pain or the neuropathic disorder.

The following 15 case reports (see Table 1) are provided in order to demonstrate and further illustrate certain preferred embodiments and aspects of the present invention and are not to be construed as limiting the scope thereof.

TABLE 1

A summary of the fifteen cases mentioned in detail below.

| Case # | Demographics | Underlying disease causing NP | NP duration prior to EGFR-I (months) | Pain Detect Score # | Worst pain 24 hrs prior to EGFR-I (0-10 NRS) | Worst pain 24 hrs after EFGR-I (0-10 NRS) | Worst pain 2 wks after EFGR-I (NRS 0-10) | Previous failed treatments | EGFR-I effective | Follow up (as of Dec. 10, 2013) |
|---|---|---|---|---|---|---|---|---|---|---|
| 1 | M, 68 yrs | Rectal cancer with sacral plexus/sciatic nerve invasion | 24 | ND | 8-10 | 0-1 | 0-1 | Paracetamol, Steroids, Opiates, Antiepileptics, Antidepressants, Chemotherapy, Palliative pelvic radiation hyperbaric oxygen | Cetuximab | 30 Jan. 2007-21 Dec. 2010 47 months |
| 2 | F, 53 yrs | CRPS type I | 8 | 31/38 | 9-10 | 0 | 0 | Paracetamol, NSIADs, Steroids, Weak | Cetuximab, Gefitinib, Panitumumab, | 13 Jan. 2012 to present 23 months |

TABLE 1-continued

A summary of the fifteen cases mentioned in detail below.

| Case # | Demo-graphics | Under lying disease causing NP | NP duration prior to EGFR-I (months) | Pain Detect Score # | Worst pain 24 hrs prior to EGFR-I (0-10 NRS) | Worst pain 24 hrs after EFGR-I (0-10 NRS) | Worst pain 2 wks after EFGR-I (NRS 0-10) | Previous failed treatments | EGFR-I effective | Follow up (as of Dec. 10, 2013) |
|---|---|---|---|---|---|---|---|---|---|---|
| | | | | | | | | opiates, Antiepileptics, Antidepressants, Nerve blocks, Clonidine, Physical therapy | Erlotinib | |
| 3 | M, 63 yrs | Failed back surgery syndrome | 8 | 26/38 | 8-10 | 0-1 | 0-1 | Antiepileptics, Opiates | Cetuximab, Gefitinib, Panitumumab | 30 Jan. 2012-24 Oct. 2012 9 months |
| 4 | M, 57 yrs | Bladder cancer with sacral plexus invasion | 6 | 24/38 | 10 | 0 | 0 | Paracetamol, Steroids, Opiates, Antiepileptics, Antidepressants, Chemotherapy, Palliative pelvic radiation | Cetuximab, Gefitinib | 10 Feb. 2012-14 Nov. 2012 9 months |
| 5 | F, 72 yrs | Phantom limb pain | 11 | 16/38 | 7-10 | 1-3 | 5 | Paracetamol, NSAIDs, Steroids, Opiates, Antiepileptics, Benzodiazepines, Physical therapy | Panitumumab, Erlotinib | 8 Jun. 2012-7 Sep. 2012 3 months |
| 6 | F, 72 yrs | Benign sciatica | 5 | ND | 7 | 0 | 0 | Paracetamol, NSAIDs, Benzodiazepines | Panitumumab | 14 May 2012 - 20 Aug. 2012 3 months |
| 7 | M, 67 yrs | CIPN | 24 | 19/38 | 8 | 8 | 7* | Antiepileptics, Paracetamol, NSAIDs | Panitumumab, Erlotinib | 28 Aug. 2012-6 Dec. 2012 3.5 months |
| 8 | F, 77 yrs | Herpetic neuralgia | 0.5 | ND | 10 | 4-5* | 4-5* | Steroids, Opiates, Antivirals | Panitumumab, Erlotinib | 31 Oct. 2012-3 Apr. 2013 5 months |
| 9 | F, 52 yrs | Failed back surgery syndrome | 8 | 28/38 | 10 | 10 | 3 | Antiepileptics, Paracetamol, NSAIDs | Erlotinib | 18 Oct. 2012 to present 14 months |
| 10 | F, 25 yrs | Renal cancer with lumbar and sacral nerve root invasion | 3 | 25/38 | 10 | 2-3 | 3 | Paracetamol, Opiates, Antiepileptics, Benzodiazepines | Panitumumab, Erlotinib | 20 Dec. 2012-12 Jul. 2013 7 months |
| 11 | M, 60 yrs | Rectal cancer with skeletal metastases | 1 | ND | 9 | 4 | 0 | Paracetamol, NSAIDs, Steroids, Opiates, Antiepileptics, Benzodiazepines, Chemotherapy | Panitumumab | 06 Sep. 2013 to present 3.5 months |
| 12 | M, 41 yrs | Inflammation of sciatic nerve | 10 | 16/38 | 7 | 2 | 4-5 | Paracetamol, NSAIDs, Steroids, Opiates, Antiepileptics, epidural and peripheral nerve blocks | Panitumumab | 17 Sep. 2013 to present 3 months |
| 13 | M, 63 yrs | CIPN | 24 | 23/38 | 8-9 | 8-9 | 4-5 | Opiates, Antiepileptics | Panitumumab, Erlotinib | 22 Oct. 2013 to present 2 months |
| 14 | F, 77 yrs | Post herpetic neuralgia | 26 | 19/38 | 8 | 5 | 6* | Paracetamol, Opiates, Antiepileptics, Benzodiazepines, Antidepressants, Capsaicin | Panitumumab, Erlotinib | 12 Nov. 2013 to present 4 weeks |
| 15 | F, 42 yrs | Cervical cancer | 6 | ND | 10 | 0 | 0 | Several, including | Panitumumab | 28 Nov. 2013 to present |

TABLE 1-continued

A summary of the fifteen cases mentioned in detail below.

| Case # | Demo-graphics | Under lying disease causing NP | NP duration prior to EGFR-I (months) | Pain Detect Score # | Worst pain 24 hrs prior to EGFR-I (0-10 NRS) | Worst pain 24 hrs after EFGR-I (0-10 NRS) | Worst pain 2 wks after EFGR-I (NRS 0-10) | Previous failed treatments | EGFR-I effective | Follow up (as of Dec. 10, 2013) |
|---|---|---|---|---|---|---|---|---|---|---|
| | | with pelvic nerve invasion | | | | | | continous intrathecal and subcutaneous morphine | | 2 weeks |

M = male;
F = female;
NP = neuropathic pain;
CRPS = complex regional pain syndrome;
hrs = hours;
CIPN = Chemotherapy induced peripheral neuropathy;
NRS = numeric rating scale;
*=shorter duration of painful bursts;
according to the Pain Detect tool, a score between 19 and 38 makes a neuropathic component of pain more than 90% probable Case 1

A 68 year old male with metastatic colon cancer suffered from neuropathic pain due to a pelvic recurrence impinging on his sciatic nerve. Over the course of several years he was treated with potent opioid analgesics, antiepileptics, antidepressants, anti-inflammatories, radiotherapy, chemotherapy, hyperbaric oxygen and acupuncture, in an attempt to relieve this pain. These treatments were only marginally effective and dose-escalation was limited by side-effects, see FIG. 1a).

After approximately three years, the patient was given the combination of XELOX chemotherapy (capecitabine and oxaliplatin) and the EGFR antibody, cetuximab, in yet another effort to shrink his pelvic tumor and thereby relieve his pain. At the outset of this treatment the patient required 200 mg dolcontin per 24 hours. At his first follow-up appointment, after two treatments, he reported that he had practically stopped all opiate use, see FIG. 1b) Table 2a).

TABLE 2a

The effect of cetuximab monotherapy during progression of rectal cancer recurrence causing neuropathic pain. a) A detailed description of the patient's clinical course during the first months of treatment (as depicted in FIG. 1d).

| Time | 0# | 4 weeks | 6 weeks | 2-4 months | 5-8 months<sup>□</sup> |
|---|---|---|---|---|---|
| Performance Status | ECOG 2 | | ECOG 0 | | ECOG 1 |
| Clinical picture | Increasing pain despite increasing morphine dose. | "A new man" Significantly less pain. Pain recurrence during last few days of each 14-day treatment cycle, necessitating increasing depot morphine. | | | Continued positive effect within hours, especially on peak pain. Continues to experience end-of-cycle failure. |
| Cetuximab intervention | Dose: 450 mg First infusion of cetuximab monotherapy given as a trial of analgesic effect. | Dose: 350 mg Third infusion | Dose: 150 mg Lower dose of cetuximab in order to assess dose-response and placebo effect. | Dose: 450 mg Continuation of 12-day cycles with cetuximab monotherapy. | Dose: 550 mg Trial of increased cetuximab dose in order to assess end-of-treatment failure. |
| Result of treatment | | Less pain within 4 hours of cetuximab infusion, lasting 2 weeks. | No resultant analgesic effect. | Less pain within 4 hours of cetuximab infusion, lasting 10-14 days. | Increased dose did not prolong the analgesic response. Interval shortened to 10-12 days. |
| 24-hour morphine | Depot: 290 mg | Depot: 150 mg | Increased morphine | Depot: 90 mg just after | Depot: 290 mg just after |

TABLE 2a-continued

The effect of cetuximab monotherapy during progression of rectal cancer recurrence causing neuropathic pain. a) A detailed description of the patient's clinical course during the first months of treatment (as depicted in FIG. 1d).

| Time | 0[#] | 4 weeks | 6 weeks | 2-4 months | 5-8 months[□] |
|---|---|---|---|---|---|
| requirement | | | requirement | infusion, 180 mg just before next dose | infusion and up to 480 mg just before next dose |
| | Immediate release: 120-180 mg | Immediate release: none | | Immediate release: none except the last few days of the cycle | |

[#]corresponds to line 1d in FIG. 1;
[□]corresponds to MRI 4 in FIG. 1 (MRI 2c in FIG. 2).

A pelvic MRI, taken four months later, showed no change in the pelvic tumor size although the neuropathic pelvic pain was completely gone at that point, see FIGS. 2a) and b).

During subsequent treatment breaks, the patient's pain recurred and he required higher doses of opioids. However, at each subsequent reintroduction of XELOX and cetuximab, analgesic response was repeated and the pain completely, or nearly completely, disappeared within four to five hours.

After 22 months of treatment with XELOX and cetuximab, the patient's lung metastases progressed and both chemotherapy and antibody treatment were discontinued, see FIG. 1c). Over the subsequent months, the patient's pain increased dramatically and his depot opioid dose escalated to 320 mg/24 hours, without satisfactory effect. After approximately four months of worsening pain, without any tumor-directed treatment, cetuximab monotherapy 450 mg i.v./250 mg per m$^2$ was reinstated in an attempt to relieve his pain. Once again, within hours after the first infusion of cetuximab, the patient's pain improved dramatically and he was able to cut his depot opioid dose in half within the subsequent four weeks, see FIG. 1d).

For the next 20 months, while his cancer was clearly in progression, the patient continued to receive cetuximab infusions roughly every 12 days for pain relief. Despite the development of symptoms and complications from his metastatic disease, the chronic pelvic neuropathic pain continued to be best controlled with cetuximab.

Importantly, in order to test whether the analgesic effect of this rather expensive medication was dose-dependent, the patient was given 20% of the normal cetuximab dose (he was unaware of this change) which resulted in no analgesic effect. The cetuximab dose was therefore increased to the previously effective dose and he continued to receive infusions approximately every 12 days, with effective analgesia reached within 4-5 hours, lasting just under 2 weeks. During the last few days before a new infusion, the patient required higher doses of opioids, but this could be reduced again to approximately ⅓rd of the dose immediately following subsequent cetuximab infusion.

Eight months after starting cetuximab monotherapy for analgesia, MRI of the pelvis showed an increase in the offending lesion, see FIG. 2c). Despite this finding, cetuximab continued to have the dramatic analgesic effect described and the patient was able to maintain a much better quality of life.

Toward the end of his life, the patient required increasing doses of depot morphine and tended to experience shorter time intervals without "unbearable" peak pain. On the day prior to his very last cetuximab infusion, which was administered after 20 months of monotherapy, the patient was admitted to hospital with intense pain. Just hours after the cetuximab infusion, the patient reported that pain at rest had been reduced from five to two and pain on movement had been reduced from nine to two on a ten-point numeric rating scale (Table 2b), without increase in analgesic medications or any other interventions. The patient died one month later.

Cases 2-15

Based on the dramatic anti-NP effect of EGFR inhibition seen in case 1 (Kersten C, Cameron M G. Cetuximab alleviates neuropathic pain despite tumour progression. BMJ Case Rep 2012; 2012), we offered treatment with intravenous (cetuximab, panitumumab) and oral (gefitinib, erlotinib) EGFR-inhibitors to six additional patients with chronic, debilitating and therapy-resistant NP. Furthermore, we observed serendipitous relief of NP in two additional patients who were being treated with EGFR-inhibitors for cancer. Below, we report the clinical course of NP relief in these eight additional patients who were suffering from various types of NP syndromes (summarized in Table 1).

EGFR-inhibitors have been widely tested in clinical trials and are approved oncologic drugs with primarily transient and manageable side-effects (Holt K. Common side effects and interactions of colorectal cancer therapeutic agents. J Pract Nurs 2011; 61:7-20; Petrelli F, Borgonovo K, Cabiddu M, Barni S. Efficacy of EGFR Tyrosine Kinase Inhibitors in Patients With EGFR-Mutated Non-Small-Cell Lung Cancer: A Meta-Analysis of 13 Randomized Trials. Clin Lung Cancer 2012; 13:107-14; Brown T, Boland A, Bagust A, et al. Gefitinib for the first-line treatment of locally advanced or metastatic non-small cell lung cancer. Health Technol Assess 2010; 14:71-9).

Two of three non-cancer patients (cases 2 and 3) and both cancer patients (cases 4 and 5) responded within 24 hours, with a mean decrease in worst pain from 9 to 1 as documented on the Brief Pain Inventory, short form (BPI) see FIG. 3. Three patients (cases 2, 4 and 5) who were taking analgesics for their NP at the time of first EGFR-inhibition, were able to reduce the doses significantly. Follow-up as of Dec. 10, 2013 is 7-666 days for those who have responded to treatment In some cases, the patients were asked to complete a BPI short form daily, just before and during the EGFR inhibition, in order to document their neuropathic pain and thus, help us to judge their responses and guide treatment decisions. The patients' scores, when available, are summarized in FIG. 3.

Case 2

Case 2 is a 53 year old female with an eight-month history of complex regional pain syndrome type 1 (CRPS1) of the right hand, see Table 1 and FIG. 4a. She had a Pain Detect score of ³¹⁄₃₈ and was totally disabled due to excruciating pain despite of extensive treatments, including nerve blocks, see table 1. The patient was given a total of six weekly infusions of cetuximab, (FIG. 3 upper panel, red arrows).

Within 24 hours after the first cetuximab dose, the patient experienced complete pain relief which persisted until the next infusion. After three weekly infusions of cetuximab, with continuous response, treatment with the monoclonal antibody panitumumab was attempted (FIG. 3, blue arrow). Due to its pharmacokinetic properties, this extracellular EGFR-inhibitor is administered biweekly. It was therefore given in an attempt to simplify the treatment procedure for the patient. However, the patient reported recurrence of severe pain on the very same evening as the panitumumab infusion. She received a therapeutically successful infusion of cetuximab on the following day. After a total of six infusions of cetuximab, EGFR-inhibition was converted to the oral small molecule inhibitor, gefitinib, so that the patient could be free to travel abroad on a holiday.

Gefitinib was started seven days after the last cetuximab infusion and the patient did not experience pain recurrence after conversion to tablets, see FIG. 3 upper panel, green arrows. Nineteen weeks after her first gefitinib dose, and 25 weeks after her first infusion of EGFR-inhibitor, the patient developed elevated liver transaminases, although her NP continued to be completely relieved. Gefitinib was discontinued and within 48 hours, the excruciating pain recurred. Intravenous panitumumab was again attempted, see FIG. 3 upper panel, blue arrow. This time she had not been given cetuximab shortly beforehand. She began to notice improvement in the neuropathic pain during the panitumumab infusion and the pain, which was 10/10 before treatment, was reduced to ⁵⁄₁₀ the next day, ³⁄₁₀ after 48 hours, and the pain was completely gone again on the third day after the panitumumab infusion, see FIG. 3 upper panel.

For practical purposes, erlotinib, an oral formulation, was chosen as maintenance treatment. The patient was pain-free upon conversion from panitumumab to erlotinib (see FIG. 3 upper panel, yellow arrow). Her pain has not recurred since, despite the fact that the dose of erlotinib was reduced to 100 mg daily.

At the present time, which is 15 months after her first erlotinib dose, 21 months after her first gefitinib dose, and 23 months after her first cetuximab infusion, the patient's NP continues to be completely resolved. Her daily dose of erlotinib has been reduced to 100 mg per day. EGFR inhibition has had no effect on the vasomotor symptoms that accompany CRPS1. However, the pain relief has enabled the patient to comply with physiotherapy, which was previously hampered by extreme levels of pain. As a consequence, there is an indirect improvement in the edema that otherwise complicates her condition and that can lead to permanent disability.

Case 3

Case 3, a 63 year old male with an eight-month history of radiculopathy due to failed back surgery syndrome (FBSS) with scar tissue formation at the L4/L5 level (see Table 1 and FIG. 4b) was given two weekly infusions of cetuximab (FIG. 3, second panel, red arrows). Within hours after the first infusion, the patient's severe and persistent pain was reduced significantly and in the following days, the NP disappeared completely. After his second dose of cetuximab, the patient waited for pain recurrence to start a new treatment. After an eleven-day cetuximab wash-out, his NP began to relapse.

At that stage, the patient converted to gefitinib tablets (FIG. 3, green arrow). His pain continued to increase for the first two days of oral treatment. However, from the third dose of gefitinib, the pain gradually improved to levels as good as those he had experienced with cetuximab. The patient's NP was so well-controlled by both cetuximab and gefitinib that he could resume his physically active outdoorsman-lifestyle. However, he developed pneumonia one month after starting gefitinib. Dyspnoea persisted after treatment of the pneumonia and interstitial lung disease (ILD) could not be excluded. Gefitinib was therefore discontinued (see FIG. 3) and NP recurred after three days. A dose of panitumumab was subsequently given and NP diminished on the very same evening and he was again free from pain.

Case 4

Case 4 is a 57 year old male with a twenty-month history of a bladder cancer recurrence invading pelvic organs, muscles and sacral nerve roots (FIGS. 4c) and d), leading to excruciating NP for the preceding six months, despite extensive treatments, see Table 1.

The patient was given cetuximab after treatment with the combination of gabapentin, amitriptyline, paracetamol, steroids, and titration to a 24-hour morphine-equivalent dose of 1800 mg failed to control his NP. Within hours after the infusion of the EGFR inhibitor, the patient experienced complete relief of his NP for the first time in over six months, see FIG. 3 third panel, red arrow. Just three days after the first cetuximab treatment, his opioid and gabapentin doses were reduced by 50%, limited by the fear of abstinence symptoms and rebound effects that can be associated with abrupt discontinuation of these substances. Cetuximab was converted to oral gefitinib at the time of the next planned treatment (FIG. 3, green arrow). Complete relief from NP was maintained through and beyond this transition. Despite progressive tumor invasion of pelvic nerves (see FIGS. 4c) and d)) his neuropathic pain continued to be completely relieved by gefitinib for 277 days of follow-up, at which point he died of bladder cancer.

Case 5

Case 5 was a 72 year old female, suffering from pancreatic cancer with liver metastases. However, her major complaint was an eleven-month history of phantom-limb pain after a below-the-knee amputation due to non-healing ulcers from peripheral vascular disease, see Table 1.

She received panitumumab while she was being treated with palliative gemcitabine for metastatic pancreatic cancer. Despite having symptomatic cancer, chronic phantom-limb pain radiating down her left leg was her major complaint. She had developed stump atrophy, contractures and pain which prohibited the use of her prosthesis. Consequently, she was confined to a wheelchair. Within hours after the infusion of panitumumab, her phantom limb pain decreased to 50% (see FIG. 3, lower panel). She subsequently required less breakthrough pain medication, was able to sleep through the night and her health-related quality of life (QOL) improved. The intensity of worst pain recurred to baseline levels after more intensive physiotherapy, but was again effectively alleviated within one day after the second infusion of panitumumab.

Erlotinib is approved for treatment of pancreatic cancer. Panitumumab was therefore replaced by erlotinib in this patient, after the analgesic response was observed. Again, the patient reported phantom-limb pain improvement with erlotinib, but this was not as clearly conveyed in her BPI scores. However, her opioid requirement diminished and she was able to use her prosthesis for the first time since her amputation. Continued swelling and contractures around her knee joint made use of the prosthesis painful, but for the first time, it was possible, because she no longer had phantom limb pain. BPI scores therefore reflect both prosthesis and stump pain and variations in abdominal pain from pancreatic cancer. Her phantom-limb pain did not increase to previous levels during the 91 days of follow up during which she was treated with EGFR-inhibitors.

Case 6

Case 6 (see Table 1), a 72-year-old patient with metastatic colon cancer (metastatic only to her lungs) was treated with palliative panitumumab monotherapy. At her first follow-up appointment, 14 days after the first infusion, she spontaneously reported that she had experienced complete relief of her intermittent sciatica, which she had had for over six months, within 24 hours of her first infusion of panitumumab. She retrospectively described the sciatica as intermittent, graded 6 to 8 on a 10-point severity scale and until treatment with the EGFR-inhibitor was begun, it was present on most days, at times greatly limiting her activities and mobility. After treatment was started, the pain did not recur and she reported that her quality of life improved significantly while she received panitumumab. Previous treatments for her neuropathic pain condition included paracetamol, NSAIDs and benzodiazepines. During panitumumab treatment she no longer required analgesics and there were no concurrent interventions or other changes in her medications. The patient was treated with panitumumab for a total of 98 days, during which time she did not experienced recurrence of her sciatica.

Case 7

Case 7 (see Table 1) had been treated with adjuvant chemotherapy including the cytotoxic platinum compound, oxaliplatin, two years prior to being referred for neuropathic pain. Although cured of colon cancer, as an artist and musician he was completely disabled by chemotherapy-induced peripheral neuropathy (CIPN) complicating his treatment. He experienced pain characterized as neuropathic, which came in bursts, with an intensity of ten out of ten, lasting for several minutes at a time, up to twenty times daily. This neuropathic pain was progressive despite treatment with pregabalin and/or gabapentin, and it was increasingly associated with tingling and numbness of his hands and feet.

The patient was given a trial of intravenous panitumumab. Two weeks after the first treatment, he reported a lower frequency of the painful bursts and their duration was reduced from several minutes to five to ten seconds. The intensity of the pain still reached a maximum of ten out of ten although it only lasted for a few seconds, representing a clinically meaningful improvement for the patient. However, due to the temporal nature of his painful episodes, the degree of pain relief, as documented in the Brief Pain Inventory (BPI), is graphically under-represented, see FIG. 5.

After four to six weeks (2-3 doses) of treatment with panitumumab, the patient reported that his pain was reduced by 60-70%. In addition, after six to eight weeks of treatment he reported that he was beginning to regain sensibility in his fingers, see FIG. 6. The patient is an artist/musician and after two years of disabling CIPN he was once again able to play the guitar after having been treated with an EGFR-inhibitor.

Case 8

Case 8 (see Table 1) developed shingles while she was being treated with panitumumab monotherapy for stage IV colon cancer. After five months of EGFR-inhibitor treatment, she developed a pruritic blistering rash along her fifth thoracic dermatome between two treatments (gradual onset between days zero and seven, Table 3).

TABLE 3

Panitumumab relieved herpetic neuralgia. After five months of treatment with panitumumab, the patient developed a reactivation of varicella-zoster viral infection in her fifth thoracic dermatome between two treatments (day zero and seven). On day 16, she reported severe pain. A new infusion of panitumumab on day 20 led to dramatic pain relief approximately 10 minutes into the infusion.

| Date | Panitumumab-infusion | Herpes Zoster Related symptoms | Other relevant medications |
| --- | --- | --- | --- |
| Day 0 | | Reduced performance status | |
| Day 7 | + | Itching and vesicles in dermatoma Th5 without signs of superinfection. | Start valacyclovir 1000 mg × 3 for 7 days |
| ca. Day 16-20 | | Bursts of severe (10/10) lancinating pain, lasting 3-4 seconds, approximately every 10 minutes, Almost no sleep for several days and severely reduced performance status. | |
| Day 20 | + | The patient fell asleep during the panitumumab infusion. For the first time in days she was able to sleep uninterrupted, for | |

TABLE 3-continued

Panitumumab relieved herpetic neuralgia. After five months of treatment
with panitumumab, the patient developed a reactivation of varicella-
zoster viral infection in her fifth thoracic dermatome between two
treatments (day zero and seven). On day 16, she reported severe
pain. A new infusion of panitumumab on day 20 led to dramatic pain
relief approximately 10 minutes into the infusion.

| Date | Panitumumab-infusion | Herpes Zoster Related symptoms | Other relevant medications |
|---|---|---|---|
| Day 21 | | an hour. When she was awoken she reported that the pain had completely resolved. Pain intensity reduced to 4-5/10, with painful bursts occurring less frequently and of shorter duration. | |
| Day 34 | + | Intensity of painful bursts, as well as their frequency and duration continue to gradually improve (since day 21). | |

At her clinic appointment on day 20, she and her daughter reported that she had had excruciating pain along the same dermatome for the proceeding 4 days. The pain had left her sleepless for almost four days. The infusion of panitumumab given that day led to complete pain relief approximately 10 minutes into the infusion and the patient finally fell asleep. When she was awakened after two hours she was completely pain free. Details surrounding the initial clinical course of her acute varicella reactivation and neuralgia are outlined in Table 3. Eventually, when the patient's cancer progressed and panitumumab was stopped, she began taking erlotinib 100 mg. After a further 30 days of this treatment, EGFR-I was stopped and her pain never recurred.

Case 9

Case 9 (see Table 1), is a previously healthy 52 year-old woman with a seven month history of severe NP due to sacral nerve root (S1) impingement from scar tissue formation (visualized on MRI) after surgery for a benign cyst at the S1 level. Nerve block had been effective for only 1-2 days. Subsequently, she was treated with gabapentin 3600 mg/daily. Her PAIN Detect score was $28/38$ (indicating a >90% probability of neuropathic pain). The patient's numeric rating scale (NRS) score for worst pain was 10/10, and $7/10$ for average pain for the four weeks prior to treatment with EGFR-inhibitor. The severe pain caused her to become increasingly physically disabled and socially isolated and she was unable to work. Inhibition of the EGF-receptor was started with 150 mg Erlotinib tablets on the Oct. 19, 2012, see FIG. 7, lower panel, yellow arrow.

On Oct. 29, 2012 she reported that the worst pain she had experienced during the proceeding 24 hours was 2-3/10, and that the least degree of pain was $0/10$, DESPITE stopping gabapentin (3600 mg/daily). This effect began after four to five days of oral treatment, as in Case 3 (also failed back surgery syndrome). The only side-effect to date has been dry skin grade II which was transient. The patient has returned to work since starting treatment with the oral EGFR-inhibitor.

Case 10

Case 10 (see Table 1) was a 25 year old female with advanced, therapy-resistant renal cancer, diagnosed in 2011. Widespread skeletal and pelvic metastases lead to progressive invasion of thoracic and lumbar nerve roots, as well as her sacral plexus, causing neuropathic pain (NP). This pain had persisted for approximately three to four months before an attempt at EGFR-inhibition was made in December, 2012. The patient's PainDetect-score prior to EGFR-inhibition was $25/38$. She experienced constant NP radiating down her left leg with an intensity of 7 on a zero to ten numeric rating scale (NRS). In addition, she experienced more intense painful bursts, lasting 1-3 hours, with a severity of 10 out of 10 on the NRS. This kept her totally disabled and limited her to only 2-3 hours of sleep per night. The desperate situation, and in particular the intense painful attacks, severely affected the mental health of both the patient and her caregivers. Pregabalin and a daily morphine dose of 420 mg failed to have a clinically significant effect on the pain. The patient had also been treated with radiotherapy, paracetamol and benzodiazepines, in addition to self-medicating with cannabis, prior to pursuing an EGFR inhibitor for relief of NP.

She scored 10 out of 10 for worst pain in the 24 hours prior to her first treatment. She was given 6 mg/kg intravenous panitumumab. On the following day, she reported that the pain intensity was reduced to 4, with a further reduction to a NRS-level of 2-3 during the following weeks. The pain recurred to levels of 9 out of 10, 15 days after the initial infusion. A second panitumumab infusion was given three weeks after the first infusion, with a similar pattern of response. For ease of administration, EGFR-I was converted to an orally administered formulation (Erlotinib 100 mg daily) 28 days after the first i.v. infusion.

The patient remained free of unbearable neuropathic pain for the remainder of her life, although progressive cancer led to increasing pain from skeletal metastases and decubital ulcers. The patient died 9 months after the initial EGFR-I, due to her progressive cancer. She experienced no grade 3 or 4 side effects of the EGFR-Is.

Case 11

Case 11 (see Table 1) is a 60 year old male with rectal cancer, metastatic to lymph nodes, liver, lungs, and bone. He was initially treated with effective first line palliative chemotherapy but upon disease progression, developed bone pain and eventually a severe neuropathic component. In addition to pain in the affected skeletal areas (primarily vertebra and pelvis), the pain increasingly radiated down his right leg as the disease progressed. CT scan demonstrated widespread tumor manifestations both in the pelvic soft-tissues and in his vertebra and bony pelvis although there was not any one clear lesion that explained the neuropathic pain. He was treated with palliative radiotherapy, NSAIDS, paracetamol, opiates, steroids and gabapentin without effect. He had recently (on Aug. 5, 2013) started second line palliative chemotherapy but his symptoms progressed during this treatment which was still in its early stages. The NP was eventually so severe that he had to be admitted to hospital for treatment. He described the pain as 9-10 out of 10 on a 0-10 NRS while being treated with 100 mg depot morphine per 24 hours, albeit with very limited effect. He refused further escalation of the morphine dose and did not use any breakthrough morphine because he felt it had no effect at all on his NP and only negatively contributed to his overall well-being.

On Sep. 6, 2013, the patient was given intravenous panitumumab 6 mg/kg in an effort to relieve his intractable NP. Approximately 12 hours after the panitumumab infusion, the patient was somnolent and clearly overdosed on opiates. He described his pain as 4 out of 10 at that point. On September 8, two days after the panitumumab infusion, the patient's NP was completely gone and he no longer required opiates.

The patient has continued to receive panitumumab every 2 weeks and his NP has not recurred. He experienced transient acne when he did not comply with prophylactic antibiotics (tetracycline) as prescribed, but has otherwise not experienced any side effects.

Case 12

Case 12 (see Table 1) is a 41 year old, previously healthy male that had experienced mild lumbar back pain for a year prior to acute onset of increased pain in the same region. A one week period without pain was then followed by sudden onset of more dramatic increase in burning pain radiating down his left leg, along dermatomes L4 and L5. MRI revealed a rupture of the annulus fibrosis of the lumbar disc between L4 and L5 and increased tissue around the dorsal L4 and L5 roots.

The radiological findings were interpreted as being the result of a spontaneous enucleation of a lumbar prolapse with resultant inflammation of the nerve root. Neurological examination confirmed L4/5 root affection.

The patient's PainDetect-score prior to EGFR-inhibition was 16/38. He described an average pain intensity of 5-6 and worst pain reaching 6-8 in the 10 months prior EGFR-I. His social life was severely disturbed and he was only able to work a 20% job. In attempts to alleviate his NP, the patient received paracetamol, NSAID's, steroids, opiates, and epidural and peripheral nerve blocks with little effect.

Ten months after the sudden worsening of NP, 6 mg/kg panitumumab i.v. was given in an attempt at pain relief. Twenty four hours after the infusion, his worst pain was reduced to two on a zero to 10 NRS. However, he increased his level of physical activity and his worst pain levels rose to five. The analgesic effect lasted only one week. After two weeks, a second infusion of panitumumab was given, followed by pain reduction again, albeit to a lesser degree. His new worst pain level was around three, despite a reduction of pregabalin from 375 mg to 225 mg. As a result, after nearly one year of 80% sick leave, he was able to return, full-time, to his previous job, eight weeks after the first infusion of panitumumab.

The patient experienced early skin rash grade 2-3. There were otherwise no reported side effects. Due to the patient's satisfaction with his improved pain and functional levels (reported pain reduction of 75%), further treatment with EGFR-I was put on hold. Three months after the initial EGFR-I administration, the patient's NP is on average 2, with occasional episodes where it peaks at 3.

Case 13

Case 13 (see Table 1) is a 63 year old male who was treated with adjuvant chemotherapy including oxaliplatin for a Dukes C colon cancer in 2010. This led to progressive chemotherapy induced peripheral neuropathy (CIPN) for a period of 2.5 years.

The patient suffered from progressive burning pain in a stocking-like distribution, from his toes up to both knees in the period after chemotherapy. This prohibited most physical activity, including walking. His PainDetect-score was 23/38. His pain score was 7-8 out of 10 when he was walking and two out of 10 at rest. In addition, he experienced 5-20 painful bursts lasting 30-60 seconds, with an intensity of ten out of ten on a 0-10 NRS. He had tried antiepileptics, paracetamol and mild opioids without clinically significant effect.

The patient was given 6 mg/kg panitumumab i.v. on Oct. 22, 2013, in attempt to alleviate his NP. After two days, he reported a 20-30% reduction in pain intensity. In addition, the distribution of the pain had been reduced, whereby the pain in the legs had completely disappeared and was only located distally in his feet. Two weeks after the panitumumab-infusion, the patient's pain was further reduced by 30-40% of baseline levels and treatment was converted to 150 mg oral erlotinib.

The patient experienced continued improvement, with relief of up to 70% over the following three weeks. At the same time, he increased his physical activity from no walking prior to EGFR-I to 30 minute daily walks and bowling two to three times per week. At present, four weeks after starting erlotinib, he has experienced a week with slightly worsening pain (only 60% pain reduction). This could be ascribed to a) increased physical activity, b) chance, c) colder weather or d) the fact that he uses omeprazole, which can interfere with the absorption of erlotinib.

Case 14

Case 14 (see Table 1) is a 77 year old female who developed post-herpetic neuralgia after an episode of thoracic herpes zoster in August, 2011. Once the rash resolved, there was initial improvement in the pain that she experienced during the acute phase of the disease. However, pain in the affected dermatome persisted and has not improved for well over a year, despite conventional treatments. Paracetamol, codeine, gabapentin, capsaicin, benzodiazepines and amitryptiline have been unable to influence the pain although she was able to sleep better with the use of the tricyclic antidepressant in combination with benzodiazepine. Her PainDetect score was 19/38. She described her pain as constant, usually around 5 out of 10, but with exacerbations reaching 10 out of 10 on a 0-10 NRS several times daily, on most days. The pain had a significantly negative impact on her quality of life and activities of daily living, as recorded on the brief pain inventory.

The patient was given an intravenous infusion of 6 mg/kg panitumumab on Nov. 12, 2013. She experienced gradual improvement in the pain, noticeable from the first day after the infusion. In the first two weeks after the infusion, her worst pain was registered at 6-7 out of 10 despite reducing her amitryptiline dose from 40 mg to 20 mg. Four weeks after the start of EGFR-I (one week after starting erlotinib) her pain continues to improve and she describes her average pain as 4 out of 10. She no longer feels that she has acute exacerbations since her maximum pain has been reduced from 10 to 6 on the 0-10 pain scale. She describes her situation as dramatically improved as she can now carry out tasks that were impossible for her during the previous two years. The pain relief has resulted in improved social functioning and quality of life and she has not experienced any side effects to date.

Case 15

Case 15 (see Table 1) is a 42 year old female with metastatic, recurrent cervical cancer, who has been treated with palliative chemotherapy for the past two years. Since the spring of 2013 she has had rapidly progressive disease. Her principle morbidity has been related to the pelvic manifestations of her recurrence which have invaded pelvic nerves, leading to excruciating NP radiating into her lower extremity. She has been treated with radiotherapy and conventional medications including paracetamol, steroids, opiates, and pregabalin, without significant effect. The pain had become so severe that she required continuous intrathecal anesthesia (marcain, fentanyl, adrenalin) in the intensive care setting. Despite this, she described the pain as unbearable and EGFR-I was therefore given.

Intravenous panitumumab 6 mg/kg was given on Nov. 28, 2013. The neuropathic pain was significantly better within hours of the infusion and for the first time in months, she could take a shower rather than a sponge-bath in bed. By the following day, the neuropathic pain was completely gone as her opiates were being titrated down. She was discharged from the intensive care unit to her home on the day after treatment. She has remained free from NP since the infusion, two weeks ago. Despite progressive cancer, she feels better today (2 weeks after treatment) than she has in the previous 6 months.

We have repeatedly witnessed the successful analgesic treatment of severe NP (both malignant and non-malignant) due to diverse long-standing pain conditions refractory to standard treatments. We suggest the effective alleviation of NP to be a class effect of EGFR-inhibitors, since all four tested drugs were effective in a manner that can be explained by the established pharmacokinetics of the used drugs. Both intravenous/extracellular (cetuximab and panitumumab) and oral/intracellular (gefitinib and erlotinib) EGFR-inhibition led to complete NP relief in conditions where both proximal and/or distal parts of peripheral nerves were affected.

Further support for a genuine drug effect is derived from the correlation between EGFR inhibitor pharmacokinetics and the clinical observations in cases 1, 3 and 9. In case 1 and 3, the pain recurred about 11-14 days after the last cetuximab infusion and roughly 20 days after panitumumab (case 3). This is consistent with the half life of these drugs (Ramanathan R K. Alternative dosing schedules for cetuximab: a role for biweekly administration? Clin Colorectal Cancer 2008; 7:364-8; Saadeh C E, Lee H S. Panitumumab: a fully human monoclonal antibody with activity in metastatic colorectal cancer. Ann Pharmacother 2007; 41:606-13).

Case 3 experienced complete washout of the iv antibody (cetuximab), with recurrence of the pain, prior to starting the oral agent gefitinib. See FIG. 3, second panel, green arrow and FIG. 7 upper panel. Although the analgesic response took longer with gefitinib (one week), it was also complete (pain score 0/10) after three weeks. In other words, the analgesic effect was as pronounced but not as rapid as with the iv agent. In Case 9 we observed the effect of treating NP with oral EGFR-inhibitor up front. The fact that these patients' pain responded more slowly to the oral drug than to intravenous administration of both cetuximab and panitumumab, supports the hypothesized causal and direct effect of EGFR inhibition.

Case 2 reported a dramatic increase in pain just hours after infusion of the anti-EGFR antibody panitumumab. A recent study has demonstrated that cetuximab and panitumumab hinder each other's EGFR binding (Alvarenga M L, Kikhney J, Hannewald J, et al. In-depth biophysical analysis of interactions between therapeutic antibodies and the extracellular domain of the epidermal growth factor receptor. Anal Biochem 2012; 421:138-51). This may possibly have led to the displacement of cetuximab by panitumumab and thereby caused the rapid pain recurrence observed in case 2. Interestingly, when the same patient was given intravenous panitumumab AFTER a washout of gefitinib (accompanied by recurrence of pain), she responded with dramatic pain relief within hours, just as she had with intravenous cetuximab. There is currently no international consensus on the pathophysiology of many NP conditions. It is therefore important to note that our fifteen cases comprise widely different NP conditions. Some have diseases with a clear affection of the proximal peripheral nerves (cases 1, 3, 4, 6, 9, 10, 12 and 15), whereas others most likely have a more distal affection (cases 7 and 13) or a mixture of both proximal and distal affection (case 2, 5, 8, 14). In none of the fifteen patients in whom we have observed an analgesic response to EGFR-inhibition, have we seen a recurrence of pain to pre-treatment levels, while they were under treatment.

We claim:

1. A method of treating a subject with pain associated with a neurological disease, wherein said treatment comprises a) at least an initial administration of an anti-epidermal growth factor receptor (EGFR) antibody or a biologically active portion thereof followed by b) administration of a small molecule inhibitor of EGFR, wherein said pain is neuropathic pain selected from the group consisting of non-compressive neuropathic pain, compressive neuropathic pain, toxic neuropathic pain, metabolic neuropathic pain, traumatic neuropathic pain, autoimmune neuropathic pain, infectious neuropathic pain, and congenital or hereditary neuropathic pain, wherein said neuropathic pain is non-cancer related.

2. The method of claim 1, wherein the pain is associated with pain nerve fiber type A, and/or B, and/or C.

3. The method of claim 1, wherein, wherein the pain is associated with myelinated nerve fibers.

4. The method of claim 1, wherein said compressive neuropathic pain is pain associated with a syndrome selected from the group consisting of failed back surgery syndrome, carpal tunnel syndrome, compartment syndrome and sciatica.

5. The method of claim 1, wherein said toxic neuropathic pain is selected from pain associated with exposure to an agent selected from the group consisting of lead, arsenic, asbestos, isoniazid and thallium.

6. The method of claim 1, wherein said metabolic neuropathic pain is selected from pain associated with painful diabetic neuropathy, nutritional deficiency, alcohol induced neuropathy and thiamine deficient axonal sensorimotor burning neuropathy.

7. The method of claim 1, wherein said traumatic neuropathic pain is associated with a syndrome selected from the group consisting of phantom limb syndrome and complex regional pain syndrome.

8. The method of claim 1, wherein said autoimmune neuropathic pain is selected from the group consisting of chronic inflammatory demyelinating polyneuropathy and vasculitic neuropathy.

9. The method of claim 1, wherein said infectious neuropathic pain is selected from the group consisting of postherpetic neuralgia and painful HIV-distal sensory polyneuropathy.

10. The method of claim 1, wherein said agent reduces or modulates symptoms of said pain, wherein said symptom is selected from the group consisting of shooting pain, burning pain, tingling, numbness and combinations thereof.

11. The method of claim 1, wherein said method provides for the long term palliative care of a subject.

12. The method of claim 11, wherein said long term palliative care is for a period selected from the group consisting of longer than six months, longer than 12 months, longer than 24 months, longer than 36 months, longer than 48 months and longer than 60 months.

13. The method of claim 1, wherein said anti-EGFR antibody is selected from the group consisting of cetuximab, matuzumab, necitumumab, nimotuzumab, panitumumab, and zalutumumab.

14. The method of claim 13, wherein said antibody is selected from the group consisting of cetuximab or panitumumab.

15. The method of claim 1, wherein the initial dose of the anti-EGFR antibody or the biologically active portion thereof causes pain reduction of 50-100% compared to an untreated subject within less than 4-8 h after administration.

16. The method of claim 1, wherein said small molecule inhibitor of EGFR is administered orally in a dose of 10-300 mg every 1-3 days.

17. The method of claim 16, wherein said administration of said small molecule inhibitor of EGFR is 50 to 300 mg in an initial dose, and 10 to 200 mg in a subsequent daily dose.

18. The method of claim 17, wherein said small molecule inhibitor of EGFR is selected from the group consisting of afatinib, erlotinib, gefitinib, lapatinib, and neratinib.

* * * * *